(12) United States Patent
Watanabe et al.

(10) Patent No.: US 9,023,743 B2
(45) Date of Patent: May 5, 2015

(54) INORGANIC FIBER STRUCTURE AND PROCESS FOR PRODUCING SAME

(75) Inventors: Rie Watanabe, Oyama (JP); Takashi Tarao, Oyama (JP); Masaaki Kawabe, Kazo (JP); Tetsu Yamaguchi, Tokyo (JP); Shinji Sakai, Toyonaka (JP); Koei Kawakami, Fukuoka (JP)

(73) Assignees: Japan Vilene Company, Ltd., Tokyo (JP); Fukuoka Prefectural Government, Fukuoka (JP); Kyushu University, National University Corporation, Fukuoka (JP)

( * ) Notice: Subject to any disclaimer, the term of this patent is extended or adjusted under 35 U.S.C. 154(b) by 276 days.

(21) Appl. No.: 13/144,632

(22) PCT Filed: Jan. 14, 2010

(86) PCT No.: PCT/JP2010/050347
§ 371 (c)(1),
(2), (4) Date: Jul. 14, 2011

(87) PCT Pub. No.: WO2010/082603
PCT Pub. Date: Jul. 22, 2010

(65) Prior Publication Data
US 2011/0274927 A1  Nov. 10, 2011

(30) Foreign Application Priority Data

Jan. 14, 2009  (JP) .................................. 2009-005678
Jul. 23, 2009  (JP) .................................. 2009-171857

(51) Int. Cl.
*B32B 5/02* (2006.01)
*B32B 17/00* (2006.01)
(Continued)

(52) U.S. Cl.
CPC ............. *D04H 1/728* (2013.01); *Y10T 428/298* (2015.01); *D04H 1/4209* (2013.01); *D04H 1/587* (2013.01); *Y10S 977/762* (2013.01)

(58) Field of Classification Search
CPC ... C04B 20/006; C04B 20/0048; B82Y 30/00; B82Y 10/00; B82Y 40/00; A61L 2400/12; B32B 2305/026; B32B 2305/20; B32B 5/022
USPC ........... 977/762; 442/172; 264/165, 465, 638, 264/639; 428/304.4
See application file for complete search history.

(56) References Cited

U.S. PATENT DOCUMENTS
2006/0188774 A1*  8/2006  Niu et al. ........................ 429/44
2007/0122687 A1   5/2007  Sakurai et al.
(Continued)

FOREIGN PATENT DOCUMENTS
CN     1878898 A    12/2006
CN     1969073 A    5/2007
(Continued)

OTHER PUBLICATIONS
International Search Report for PCT/JP2010/050347 dated Feb. 9, 2010.

*Primary Examiner* — Matthew Matzek
(74) *Attorney, Agent, or Firm* — Heslin Rothenberg Farley & Mesiti P.C.

(57) ABSTRACT

An inorganic fiber structure comprising inorganic nanofibers having an average fiber diameter of 3 μm or less, in which an entirety including the inside thereof is adhered with an inorganic adhesive, and the porosity thereof is 90% or more, is disclosed. Furthermore, a process for producing an inorganic fiber structure is disclosed, which includes (i) a step of spinning inorganic fibers by an electrospinning method, from a spinning inorganic sol solution containing a compound mainly composed of an inorganic component; (ii) a step of forming an inorganic fiber aggregate by irradiating the inorganic fibers with ions having a polarity opposite to that of the inorganic fibers to accumulate the inorganic fibers; and (iii) a step of forming an inorganic fiber structure adhering to the inorganic fiber aggregate with an inorganic adhesive in an entirety including the inside thereof, in which an adhering inorganic sol solution containing a compound mainly composed of an inorganic component is imparted to an entirety including the inside of the inorganic fiber aggregate, and an excess adhering inorganic sol solution is removed by gas-through.

14 Claims, 9 Drawing Sheets

(51) Int. Cl.
  *B29C 39/14* (2006.01)
  *B29C 41/24* (2006.01)
  *B29C 47/00* (2006.01)
  *D04H 1/728* (2012.01)
  *D04H 1/4209* (2012.01)
  *D04H 1/587* (2012.01)

(56) References Cited

U.S. PATENT DOCUMENTS

2007/0289275 A1* 12/2007 Ohno et al. .................. 55/523
2008/0070037 A1* 3/2008 Nonokawa et al. .......... 428/401
2008/0138697 A1 6/2008 Asada et al.

FOREIGN PATENT DOCUMENTS

| | | |
|---|---|---|
| CN | 101006211 A | 7/2007 |
| EP | 1 264 804 A1 | 11/2002 |
| EP | 1 767 675 A1 | 3/2007 |
| EP | 1 925 701 A1 | 5/2008 |
| JP | 55-163248 A | 12/1980 |
| JP | 62-196342 A | 8/1987 |
| JP | 2003-73964 A | 3/2003 |
| JP | 2004-238749 | 8/2004 |
| JP | 2005-264374 | 9/2005 |
| JP | 2007063683 | 3/2007 |
| JP | 2007-217826 A | 8/2007 |
| JP | 2007-217836 A | 8/2007 |
| JP | 2007-231505 A | 9/2007 |
| JP | 2007-319074 A | 12/2007 |
| JP | 2008-199897 A | 9/2008 |
| JP | 2010-185164 | 8/2010 |
| WO | WO2005/086265 | 9/2005 |

* cited by examiner (a)

(b)

INORGANIC FIBER STRUCTURE AND PROCESS FOR PRODUCING SAME

CROSS REFERENCE TO RELATED APPLICATIONS

This application is a national stage filing under section 371 of International Application No. PCT/JP2010/050347 filed on Jan. 14, 2010, and published in Japanese on Jul. 22, 2010 as WO 2010/082603 and claims priority of Japanese application no. 2009-005678 filed on Jan. 14, 2009 and Japanese application no. 2009-171857 filed on Jul. 23, 2009, the entire disclosure of these applications being hereby incorporated herein by reference.

TECHNICAL FIELD

The present invention relates to an inorganic fiber structure (in particular, an inorganic fiber structure with functionality), and a process for producing the same. An inorganic fiber structure of the present invention can be used in, for example, a cell culture carrier, a scaffold, an antibacterial material, and the like.

BACKGROUND ART

So far, according to an electrospinning method, a non-woven fabric, in which fibers having a uniform fiber diameter form a three-dimensional network structure, and pore diameters are uniform, can be produced.

The electrospinning method like this is a method of spinning, in which while a spinning stock solution is fed to a spinning space, an electric field is applied to the fed spinning stock solution to draw and accumulate on a counter electrode. Like this, fibers drawn and spun by the action of an electric field are accumulated on the counter electrode directly by a force of an electric field; accordingly, a paper-like nonwoven fabric is formed. However, when the nonwoven fabric is used as a heat insulating material, a filter, and the like, a bulky nonwoven fabric is preferred.

Accordingly, the present applicant has proposed a process for producing a bulky nonwoven fabric (=neutralization spinning method, see patent literatures 1 and 2), which includes a step of electrifying a spinning polymer solution, a step of supplying the electrified polymer solution into a spinning space to fly by an electrostatic force, a step of irradiating the supplied and formed fibers with ions having a polarity opposite to that of the fibers, and a step of collecting spun fibers.

Since the bulky nonwoven fabric is a down-like nonwoven fabric having low density, where fibers do not adhere to each other, or, adhere very weakly to each other; it can be used in applications where a shape-retaining property and a mechanical strength are not required. However, in the application such as liquid filtration, where the shape-retaining property and mechanical strength are necessary, in some cases, a nonwoven fabric form could not be maintained to result in inadequacy in practical use.

Therefore, as a method of imparting the shape-retaining property and mechanical strength to neutrally spun inorganic fiber nonwoven fabric, for example, methods such as shown below can be considered.
(1) A method where inorganic fibers are papermade to form an inorganic fiber nonwoven fabric
(2) A method where a binder is sprayed to an inorganic fiber nonwoven fabric and dried
(3) A method where an inorganic fiber nonwoven fabric is dipped in a binder bath, followed by passing through a two-roll press (an apparatus for applying pressure) to remove an excess binder, further followed by drying However, according to the method of (1), it is very difficult to wet-lay nanofibers manufactured by the electrostatic spinning method. According to the method of (2), it is difficult to uniformly impart a binder over an entirety of the inorganic fiber nonwoven fabric (in particular, extend to the inside of the nonwoven fabric) to result in poor mechanical strength. According to the method of (3), gaps of the inorganic fiber nonwoven fabric are collapsed to result in incapability of maintaining the bulkiness and in low porosity.

Now, a fiber structure including the inorganic fiber nonwoven fabric like this can be used as a culture carrier. In order to culture cells in the state close to an environment in a living body, there is a tissue formation induction technique by three-dimensionally culturing cells. As the culture carriers, a film, a particle, a hollow fiber, a fiber aggregate, and a foam are well known.

However, these culture carriers are insufficient in surface area that is a scaffold of cells necessary for three-dimensional cultivation; accordingly, in many cases, high density cultivation of cells is difficult and a tissue formation function of cells, which is similar to an in vivo environment is not possessed.

As a culture carrier that can solve such problems of an existing culture carrier and can be three-dimensionally cultured, "a scaffold including nanofibers prepared by an electrospinning method" has been proposed (Patent literature 3). In specific examples, nanofibers made of silica or PVA are used.

However, even the scaffold including nanofibers like this is low in a cell proliferative potential and difficult to culture densely, in addition, also a cell function was difficult to develop. Furthermore, fiber density and thickness are difficult to control, and clusters of cells are irregularly formed; accordingly, it was difficult to observe a culture state.

Still furthermore, in order to impart a function to a fiber structure, a metal ion-containing compound is imparted. When, for example, calcium that engages with a broad range of biological reactions such as cell division, proliferation and differentiation, clotting of blood, muscle contraction, excitation of nerve sensory cells, phagocytosis, antigen recognition, immune reaction such as antibody secretion, and secretions of various kinds of hormones, and forms a hydroxyapatite crystal together with phosphorus to precipitate to matrix structures of bone and tooth to impart mechanical strength; sodium that works for maintaining osmotic pressure of extracellular liquid; iron that is an indispensable site of an electron carrier (cytochrome C) in transportation of oxygen and energy metabolism; magnesium that is an important inorganic component of bone and tooth; potassium that works for maintaining nervous excitement, muscle contraction, and maintaining osmotic pressure inside of cells; or metals such as copper, iodine, selenium, chromium, zinc, and molybdenum are imparted to a fiber structure, the fiber structure can be used as a cell culture substrate that can improve a cell function, or a fiber structure having antibiotic properties.

For example, in patent literature 3, "a scaffold including nanofibers surface-modified with a cell attachment factor (in particular, calcium phosphate) prepared by an electrospinning method" (claims 1, 8, and 9) has been proposed. Specifically, it is disclosed that silica nanofibers synthesized according to a sol-gel method is preferred, an adhesion rate of cells can be controlled by making hydrophilic or hydrophobic depending on a heat temperature of silica nanofibers, and phosphorus lime can be precipitated on a surface of nanofibers by incubating silica nanofibers in a simulated body liquid to be useful as an artificial bone cell carrier (paragraphs 0015, 0018, 0025, and the like).

However, a scaffold including nanofibers like this was low in cell function.

CITATION LIST

Patent Literature

[Patent literature 1] Japanese Unexamined Patent Publication (Kokai) No. 2004-238749
[Patent literature 2] Japanese Unexamined Patent Publication (Kokai) No. 2005-264374
[Patent literature 3] Japanese Unexamined Patent Publication (Kokai) No. 2007-319074

SUMMARY OF INVENTION

Technical Problem

The present invention is directed to solve the problems of prior art to provide a bulky inorganic fiber structure that can be used also in applications where a shape-retaining property and mechanical strength are necessary, an inorganic fiber structure, that is, because of being excellent in the foregoing performance, high in cell proliferation capability, can be cultured with high density, can readily develop also a cell function, can control fiber density and thickness, and is easy to observe a culture state, an inorganic fiber structure that is excellent in functionality such as being high in cell function and excellent in antibiotic properties, and a process for producing the same.

Solution to Problem

The present invention relates to
(1) an inorganic fiber structure comprising an inorganic nanofiber having an average fiber diameter of 3 μm or less, wherein an entirety including the inside of the inorganic fiber structure is adhered with an inorganic adhesive and the porosity of the inorganic fiber structure is 90% or more;
(2) the inorganic fiber structure according to (1), wherein a tensile rupture strength is 0.2 MPa or more;
(3) the inorganic fiber structure according to (1) or (2), wherein the amount of hydroxyl groups per unit weight of fiber is 50 μmol/g or more;
(4) the inorganic fiber structure according to any one of (1) to (3), wherein an inorganic fiber aggregate produced by at least a step where inorganic fibers spun by an electrospinning method are irradiated with ions having a polarity opposite to that of the inorganic fibers to accumulate the inorganic fibers, is adhered with an inorganic adhesive in an entirety including the inside thereof;
(5) the inorganic fiber structure according to any one of (1) to (4), wherein a film is not formed between the inorganic fibers;
(6) an inorganic fiber structure having functionality, wherein a metal ion-containing compound is imparted to the inorganic fiber structure according to any one of (1) to (5);
(7) the inorganic fiber structure according to any one of (1) to (6), which is used as a culture carrier;
(8) A process for producing an inorganic fiber structure, comprising:
(i) spinning inorganic fibers by an electrospinning method from a spinning inorganic sol solution containing a compound mainly composed of an inorganic component,
(ii) forming an inorganic fiber aggregate by irradiating the inorganic fibers with ions having a polarity opposite to that of the inorganic fibers to accumulate the inorganic fibers, and
(iii) forming an inorganic fiber structure adhering to the inorganic fiber aggregate with an inorganic adhesive in an entirety including the inside thereof, where an adhering inorganic sol solution containing a compound mainly composed of an inorganic component is imparted to an entirety including the inside of the inorganic fiber aggregate, and an excess adhering inorganic sol solution is removed by gas-through;
(9) the process for producing an inorganic fiber structure according to (8), wherein a heat treatment is conducted after the inorganic fiber aggregate is formed, in step (ii);
(10) the process for producing an inorganic fiber structure according to (9), wherein a heat treatment temperature is 500° C. or less;
(11) the process for producing an inorganic fiber structure of any one according to (8) to (10), wherein after the excess adhering inorganic sol solution is removed by gas-through, a heat treatment is conducted, in (iii);
(12) the process for producing an inorganic fiber structure according to (11), wherein a heat treatment temperature is 500° C. or less;
(13) the process for producing an inorganic fiber structure according to any one of (8) to (12), wherein the spinning inorganic sol solution and/or the adhering inorganic sol solution contains a metal ion-containing compound; and
(14) the process for producing an inorganic fiber structure according to any one of (8) to (13), wherein after step (iii) is conducted, a solution containing a metal ion-containing compound is imparted to the inorganic fiber structure.

As used herein, the term "nanofiber" refers to a fiber having an average fiber diameter of 3 μm or less.

Advantageous Effects of Invention

The inventive inorganic fiber structure of the invention of (1) is adhered with an inorganic adhesive over an entirety including the inside thereof; accordingly, a shape-retaining property is excellent and the mechanical strength is sufficient. In particular, also in a liquid, the shape-retaining property is excellent and the mechanical strength is sufficient. In addition, because the porosity of the inorganic fiber structure is 90% or more, the inorganic fiber structure can be used in an application where bulkiness is preferable such as a heat insulating material, a filter, a culture carrier of cells and the like, a scaffold, and an antibacterial material.

According to the preferable embodiment of the invention of (2), the tensile rupture strength is 0.2 MPa or more; accordingly, the shape-retaining property is excellent and the mechanical strength is sufficient.

According to another preferable embodiment of the invention of (3), an amount of hydroxyl groups per unit weight of fiber is 50 μmol/g or more; accordingly, apatite and the like can be precipitated on a fiber surface to be able to impart a function to the inorganic fiber structure.

According to a still another preferable embodiment of the invention of (4), a fiber spun by an electrospinning method is used. As the result thereof, a fiber diameter is thin and a surface area is large. In addition, since a pore diameter distribution is sharp, a uniform space is present inside of the inorganic fiber structure. As the result thereof, a function can be sufficiently exerted. For example, when the inorganic fiber structure is used as a culture carrier, a surface area, that is, a scaffold of cells is large; accordingly, three-dimensional culture in a large and uniform space can be conducted. In addition, an adhering efficiency between a cell and a fiber that is a scaffold with the cell is improved, and, a feed efficiency of a nutrient and oxygen indispensable for the cells is improved; accordingly, the cell proliferability is excellent and high density culture can be conducted.

Furthermore, as the result of high porosity (bulkiness) of 90% or more derived from a neutralization spinning method where an inorganic fiber aggregate is formed by irradiating an inorganic fiber with ions having a polarity opposite to that of the inorganic fiber to accumulate, the fiber density is low; accordingly, the inside of the inorganic fiber structure can be effectively used. For example, when the inorganic fiber structure is used as a culture substrate, since the fiber density is low, an advantage that cells can readily spread into the inside of the culture carrier is exerted. Further, since the inorganic fiber aggregate is formed by irradiating an inorganic fiber ions having a polarity opposite to that of the inorganic fiber to accumulate, the inorganic fiber aggregate is bulky, and the fiber density and thickness can be controlled to the observable level. Furthermore, as the result of irradiation with ions having a polarity opposite to that of the fiber, an inorganic fiber aggregate with high porosity of 90% or more is obtained.

Still furthermore, because of the inorganic fiber aggregate, a thickness is not collapsed when an inorganic adhesive is imparted. As the result thereof, the fiber density and thickness can be controlled. Accordingly, when the inorganic fiber structure is used as a culture substrate, a culture state can be readily observed.

Furthermore, since the inorganic fiber structure is adhered with an inorganic adhesive, a shape can be maintained under various service conditions such as in a solution or the like; accordingly, the inside of the inorganic fiber structure can be efficiently used. When the inorganic fiber structure is used as a culture substrate, since three-dimensional culture can be conducted, that is, cells are cultured in a state close to a tissue environment, a cell function can be readily developed.

Furthermore, an entirety including the inside of the inorganic fiber structure is adhered with an inorganic adhesive; accordingly, the porosity of 90% or more can be retained. For example, when the inorganic fiber structure is used as a culture carrier, a feed efficiency of a nutrient and oxygen indispensable for cells can be improved, and, since a scaffold necessary for cell culture is abundant, high density culture can be conducted.

According to a still another preferable embodiment of the invention of (5), an entirety including the inside of the inorganic fiber structure, without forming a film between the inorganic fibers, is adhered with an inorganic adhesive; accordingly, the porosity of 90% or more can be retained. For example, when the inorganic fiber structure is used as a culture carrier, a feed efficiency of a nutrient and oxygen indispensable for cells can be improved, and, since a scaffold necessary for cell culture is abundant, high density culture can be conducted.

According to a still another preferable embodiment of the invention of (6), since a metal ion-containing compound is imparted and contained, the inorganic fiber structure is excellent in functionality such as being high in cell function and excellent in antibiotic property.

According to a still another preferable embodiment of the invention of (7), when the inorganic fiber structure of the present invention is used as a culture carrier, since an average fiber diameter is such thin as 3 μm or less, a surface area is large. As the result thereof, an adhering efficiency between a cell and a fiber that is a scaffold with the cell is improved, and, a feed efficiency of a nutrient and oxygen indispensable for cells is improved; accordingly, the cell proliferability is excellent and high density culture can be conducted.

Furthermore, since the inorganic fiber structure is adhered with an inorganic adhesive, even in a culture solution, a shape can be maintained. As the result thereof, a bulky structure of the inorganic fiber structure can be maintained; accordingly, the culture can be three-dimensionally conducted, that is, cells can be cultured in a state close to a tissue environment; accordingly, a cell function can be readily developed.

According to a producing method of the invention of (8), the inorganic fiber structure of the present invention can be produced. In particular, since an excess adhering inorganic sol solution is removed by gas-through, while maintaining a bulky state where an entirety including the inside is adhered with an inorganic adhesive without forming a film between inorganic fibers, an inorganic fiber structure excellent in shape-retaining property and mechanical strength can be produced.

According to a preferable embodiment of the invention of (9), in the step (ii) of forming an inorganic fiber aggregate, an inorganic fiber aggregate is formed and a heat treatment is applied thereto; accordingly, a structure and heat resistance of the inorganic fiber structure can be stabilized.

According to a still another preferable embodiment of the invention of (10), a heat treatment temperature is 500° C. or less; accordingly, the hydrophilicity of the inorganic fiber structure can be increased. In addition, when the inorganic fiber structure is used as a culture substrate, cells can be readily cultured in spheroid form.

According to a still another preferable embodiment of the invention of (11), in the step (iii) of forming an inorganic fiber structure, after an excess adhering inorganic sol solution was removed by gas-through, a heat treatment is conducted; accordingly, mechanical strength and heat resistance of the inorganic fiber structure are improved.

According to a still another preferable embodiment of the invention of (12), a heat treatment temperature is 500° C. or less; accordingly, the hydrophilicity of the inorganic fiber structure can be increased. In addition, when the inorganic fiber structure is used as a culture substrate, cells can be readily cultured in spheroid form.

According to a still another preferable embodiment of the invention of (13), the spinning inorganic sol solution and/or adhering inorganic sol solution contains a metal ion-containing compound; accordingly, an inorganic fiber structure that contains a metal ion-containing compound, and is excellent in the functionality such as being high in cell function, being excellent in the antibiotic property, and the like, can be produced.

According to a still another preferable embodiment of the invention of (14), a solution that contains a metal ion-containing compound is imparted to an inorganic fiber structure; accordingly, an inorganic fiber structure that contains a metal ion-containing compound and is excellent in the functionality such as being high in cell function, excellent in antibiotic property, and the like, can be produced.

DESCRIPTION OF EMBODIMENTS

Hereinafter, with reference to attached drawings, a producing method of the present invention will be described, and an inorganic fiber structure of the present invention will be described.

A producing method of the present invention includes
(1) a step of spinning inorganic fibers from a spinning inorganic sol solution containing a compound mainly composed of an inorganic component by an electrospinning method (a spinning step),
(2) a step of forming an inorganic fiber aggregate by irradiating the inorganic fibers with ions having a polarity opposite to that of the inorganic fibers to accumulate the inorganic fibers (accumulation step), and
(3) a step of imparting an adhering inorganic sol solution containing a compound mainly composed of an inorganic component to an entirety including the inside of the inorganic fiber aggregate, removing an excess adhering inorganic sol solution by gas-through, and forming an inorganic fiber structure where an entirety including the inside is adhered with an inorganic adhesive, and,
as required, can include
(4) a step of imparting a solution containing a metal ion-containing compound to the inorganic fiber structure to impart the functionality to the inorganic fiber structure (a step of imparting a solution containing a metal ion-containing compound).

In a producing method of the present invention, in place of the step of imparting a solution containing a metal ion-containing compound (4), or, in addition to the step (4), a metal ion-containing compound can be added to the spinning inorganic sol solution used in the spinning step (1), and/or, to an adhering inorganic sol solution used in the adhering step (3).

Figure 1:
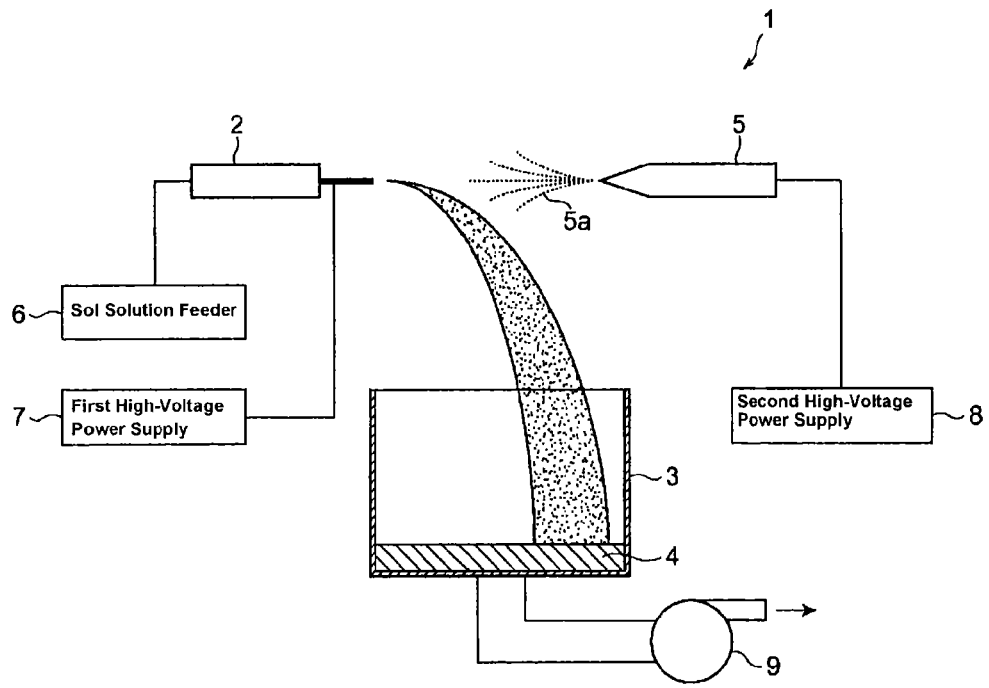
FIG. 1 is a schematic illustration illustrating one embodiment of an electrospinning apparatus that can conduct a spinning step (1) and an accumulation step (2) in the producing method of the present invention.

FIG. 1 is a schematic illustration illustrating one embodiment of an electrospinning apparatus that can conduct a spinning step (1) and an accumulation step (2) in the producing method of the present invention.

In FIG. 1, an electrospinning apparatus 1 includes a spinning nozzle 2 that discharges a spinning inorganic sol solution containing a compound mainly composed of an inorganic component that is a raw material of fiber, and a collecting member (for example, a net, a conveyer, and the like) 4 disposed inside of a fiber collecting box 3 that is a fiber collecting apparatus disposed on the lower side of a tip of the spinning nozzle 2. Furthermore, the electrospinning apparatus 1 includes an counter electrode 5 that is disposed facing to the spinning nozzle 2, generates ions having a polarity opposite to that of the fiber discharged to form, and can electrically attract fiber. To the spinning nozzle 2, a sol solution feeder 6 that feeds a spinning inorganic sol solution is connected, and, to the spinning nozzle 2 and the counter electrode 5, a first high voltage power supply 7 and a second high voltage power supply 8 are connected, respectively. Furthermore, to the fiber collecting box 3, a suction machine 9 that sucks the fiber into the fiber collecting box 3 is disposed.

Figure 2:
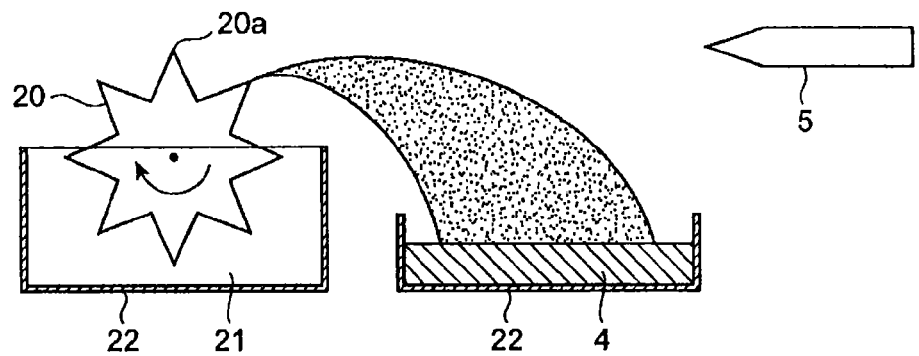
FIG. 2 is a schematic illustration illustrating an electrode with knife edges dipped in a spinning inorganic sol solution.
Figure 3:
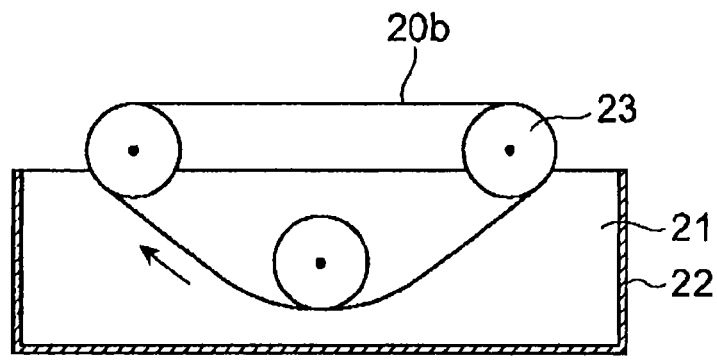
FIG. 3 is a schematic illustration illustrating a conveyer-like wire electrode dipped in a spinning inorganic sol solution.

As the spinning nozzle 2, a metal or nonmetal pipe having an inner diameter of about 0.01 to 5 mm can be used. Furthermore, as illustrated in FIG. 2, a rotating saw teeth gear 20 is dipped in a sol solution vessel 22 that accommodates a spinning inorganic sol solution 21, and an edge electrode where a tip portion 20a of the saw teeth gear 20 facing the counter electrode 5 is an electrode can be used. As illustrated in FIG. 3 in a similar manner, with a wire 20b rotated inside of the sol solution vessel 22 by a roller 23, a conveyer-like wire 20b to which the spinning inorganic sol solution 21 adhered can also be used as an electrode. In FIG. 3, a counter electrode (not illustrated in the drawing) is disposed vertically to a plane of paper. Furthermore, also conventional various kinds of electrospinning electrodes can be used.

Figure 4:
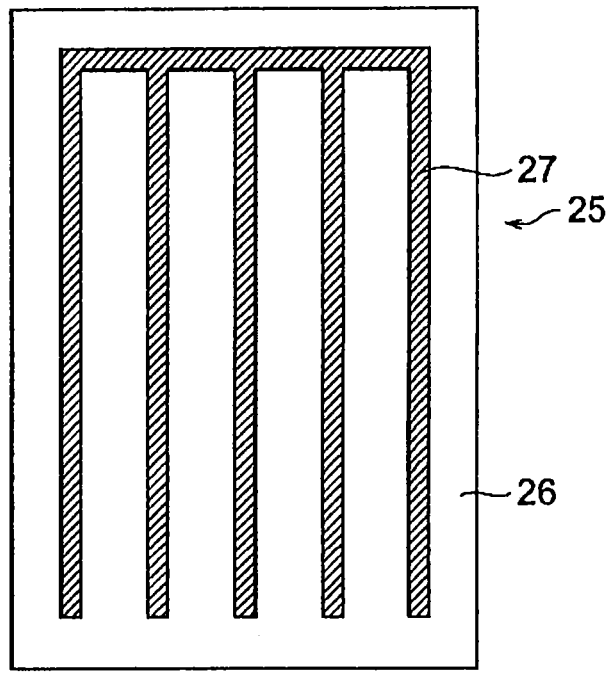
FIG. 4(a) is a plan view schematically illustrating a structure of a creeping discharge element.
FIG. 4(b) is a side view schematically illustrating a structure of a creeping discharge element.
Figure 4:
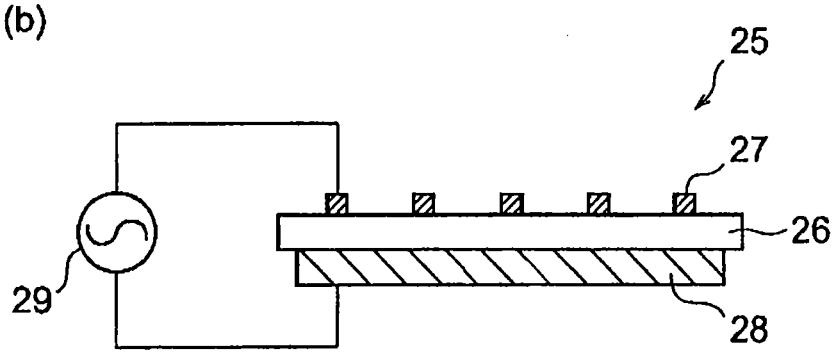

As the counter electrode 5, a corona discharge needle (with a high voltage applied or grounded), a corona discharge wire (with a high voltage applied or grounded), an AC discharge element or the like can be used. Furthermore, as the AC discharge element, a creeping discharge element illustrated in FIG. 4 can be used. That is, in FIG. 4, in the creeping discharge element 25, a discharge electrode 27 and an induction electrode 28 are disposed with a dielectric substrate 26 (for example, alumina film) sandwiched therebetween, an AC high voltage is applied between these electrodes to cause a creeping discharge at a portion of the discharge electrode 27, thereby positive and negative ions can be generated.

In the spinning step (1), firstly, (1) a step of forming a spinning inorganic sol solution containing a compound mainly composed of an inorganic component is conducted. In the present description, "being mainly composed of an inorganic component" means that an inorganic component is contained in an amount of 50% by mass or more, being contained in an amount of 60% by mass or more is more preferable, and being contained in an amount of 75% by mass or more is more preferable.

The spinning inorganic sol solution can be obtained by hydrolyzing and polycondensating at a temperature of about 100° C. or less a solution (stock solution) containing a compound that contains elements constituting an inorganic fiber obtained finally according to a producing method of the present invention. A solvent of the stock solution is, for example, an organic solvent (for example, alcohol) or water.

Examples of the elements constituting the compound include, without particularly restricting, lithium, beryllium, boron, carbon, sodium, magnesium, aluminum, silicon, phosphorus, sulfur, potassium, calcium, scandium, titanium, vanadium, chromium, manganese, iron, cobalt, nickel, copper, zinc, gallium, germanium, arsenic, selenium, rubidium, strontium, yttrium, zirconium, niobium, molybdenum, cadmium, indium, tin, antimony, tellurium, cesium, barium, lanthanum, hafnium, tantalum, tungsten, mercury, thallium, lead, bismuth, cerium, praseodymium, neodymium, promethium, samarium, europium, gadolinium, terbium, dysprosium, holmium, erbium, thulium, ytterbium, lutetium, and the like.

Examples of the compounds include, for example, oxides of the foregoing elements, specifically, $SiO_2$, $Al_2O_3$, $B_2O_3$, $TiO_2$, $ZrO_2$, $CeO_2$, $FeO$, $Fe_3O_4$, $Fe_2O_3$, $VO_2$, $V_2O_5$, $SnO_2$, $CdO$, $LiO_2$, $WO_3$, $Nb_2O_5$, $Ta_2O_5$, $In_2O_3$, $GeO_2$, $PbTi_4O_9$, $LiNbO_3$, $BaTiO_3$, $PbZrO_3$, $KTaO_3$, $Li_2B_4O_7$, $NiFe_2O_4$, $SrTiO_3$, and the like. The inorganic component may be constituted of a mono-oxide or a binary or more oxide. For example, the inorganic component can be constituted of two components of $SiO_2$—$Al_2O_3$.

It is necessary that the spinning inorganic sol solution has the viscosity that enables to spin fibers in a step where fibers are formed, which will be described below. The viscosity of the spinning inorganic sol solution is not particularly restricted as long as it allows to spin. However, the viscosity is preferably 0.1 to 100 poises, more preferably 0.5 to 20 poises, particularly preferably 1 to 10 poises, and most preferably 1 to 5 poises. This is because, when the viscosity exceeds 100 poises, it is difficult to spin fibers having a fine diameter, and, when the viscosity is less than 0.1 poise, there is a tendency to be difficult to obtain a fiber shape. In the case where a nozzle is used, when an atmosphere in a nozzle tip portion is set to a solvent gas atmosphere similar to that of a stock solution, in some cases, even a spinning inorganic sol solution of which viscosity exceeds 100 poises can be used to spin.

The spinning inorganic sol solution used in the spinning step (1) may contain an organic component in addition to the inorganic components such as mentioned above. Examples of the organic component include a silane coupling agent, an organic low molecular weight compound such as a dye, an organic polymer such as polymethyl methacrylate, and the like. More specifically, when a compound contained in the stock solution is a silane compound, a polymerized silane compound obtained by polycondensating a silane compound organically modified with a methyl group or an epoxy group may be contained.

The stock solution may contain a solvent (for example, an organic solvent (for example, alcohols such as ethanol, dimethyl formaldehyde) or water) for stabilizing a compound contained in the stock solution, water for hydrolyzing a compound contained in the stock solution, and a catalyst (for example, hydrochloric acid, nitric acid and the like) for smoothly promoting a hydrolysis reaction. Furthermore, the stock solution may contain an additive such as a chelating agent for stabilizing a compound, a silane coupling agent for stabilizing the compound, a compound capable of imparting various kinds of functions such as piezoelectricity, an organic compound (for example, polymethyl methacrylate) for improving the adhesiveness and controlling the compliance and the stiffness (brittleness), or a dye. These additives can be added before hydrolysis, during hydrolysis, or after hydrolysis.

Furthermore, the stock solution can contain inorganic or organic fine particles. Examples of the inorganic fine particles include titanium oxide, manganese dioxide, copper oxide, silicon dioxide, activated carbon and metal (for example, platinum). Examples of the organic fine particles include a dye, a pigment or the like. Furthermore, though the average particle size of the fine particles is not particularly restricted, it is preferably 0.001 to 1 μm, and more preferably 0.002 to 0.1 μm. By containing such fine particles, an optical function, a porosity, a catalyst function, an adsorption function, an ion exchange function, or the like can be imparted. Still furthermore, the stock solution may contain a metal ion-containing compound detailed in a step of imparting a solution containing a metal ion-containing compound (4) that will be detailed below, or may not contain.

In the case of tetraethoxysilane, when an amount of water exceeds 4 times (molar ratio) an amount of alkoxide, it is difficult to obtain a spinnable sol solution; accordingly, an amount of water is preferable to be 4 times or less an amount of alkoxide.

When a base is used as a catalyst, it is difficult to obtain a spinnable sol solution; accordingly, it is preferable that a base is not used.

A reaction temperature may be the same with or less than a boiling point of a solvent used. However, when a reaction temperature is low, a reaction speed is adequately slow to readily form a spinnable sol solution. When the reaction temperature is too low, a reaction is difficult to proceed; accordingly, the reaction temperature is preferable to be 10° C. or more.

A step of forming an inorganic fiber aggregate with the electrospinning apparatus 1 mentioned above, that is, a spinning step (1) and an accumulation step (2), are conducted as illustrated below. Firstly, a spinning inorganic sol solution that becomes a raw material of a fiber to be spun is fed from a sol solution feeder 6 to a spinning nozzle 2. Next, with a high voltage applied between the spinning nozzle 2 and the counter electrode 5, a spinning inorganic sol solution is discharged from a tip of the spinning nozzle 2. Thereby, a charged liquid sol solution, after volatilization of the solvent, coagulates to be gel inorganic fibers, and goes toward the counter electrode 5 (spinning step (1)). At this time, from the counter electrode 5 disposed facing to the spinning nozzle 2, ions 5a are irradiated toward the fibers. The charge of the fibers is neutralized with the ions, a flying force owing to an electrostatic force is lost, and the fibers fall by gravity or light wind and are recovered in the fiber collecting box 3. Accordingly, a low density and down-like inorganic fiber aggregate can be obtained (accumulation step (2)).

Generation and irradiation of the ions can be conducted continuously or discontinuously. Furthermore, an electric field may be generated between the spinning nozzle 2 and the counter electrode 5, that is, a high voltage may be applied to either one thereof, and the other may be grounded. The spinning nozzle 2 may be heated or may not be heated.

Figure 5:
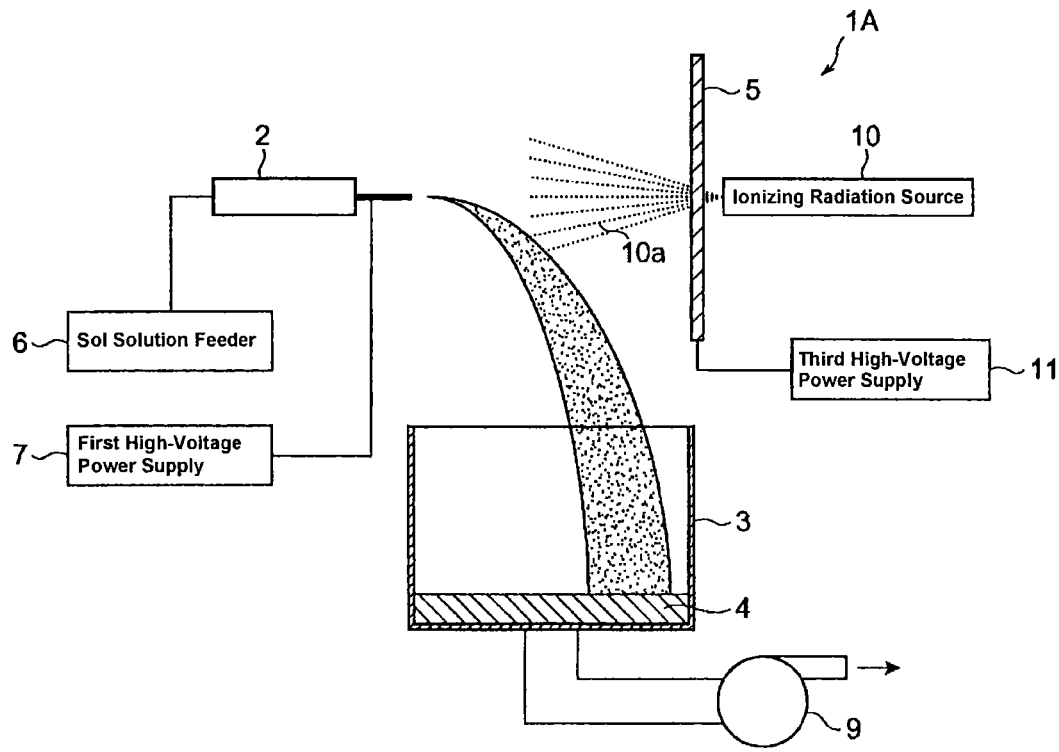
FIG. 5 is a schematic illustration illustrating another embodiment of an electrospinning apparatus that can conduct a spinning step (1) and an accumulation step (2) in the producing method of the present invention.

FIG. 5 is a schematic illustration illustrating another embodiment of an electrospinning apparatus that can conduct a spinning step (1) and an accumulation step (2) in the producing method of the present invention.

In FIG. 5, an electrospinning apparatus 1A is constituted similarly with the electrospinning apparatus 1 except that, in place of the counter electrode 5 that can generate ions and can attract the fibers in Example 1, an ionizing radiation source 10 capable of irradiation of ionizing radiation, and a net-shaped counter electrode 5 that can attracts fibers (connected to a third high voltage power supply 11) are used; accordingly, duplicated explanations will be omitted.

In the electrospinning apparatus 1A, predetermined voltages are applied to the spinning nozzle 2 and/or counter electrode 5 with a first high voltage power supply 7 and/or a third high voltage power supply 11 to generate a potential difference between the spinning nozzle 2 and the counter electrode 5 to electrically attract the fibers, and thereby the fibers are flied toward the counter electrode 5 (spinning step (1)). When the flying fibers are irradiated with ionizing radiation 10a, a gas is ionized and used as an ion source. Thereby, the charge of the fibers is neutralized, a flying force owing to an electrostatic force is lost, and the fibers fall by gravity or light wind and are recovered in the fiber collecting box 3. Accordingly, a low density and down-like inorganic fiber aggregate can be obtained (accumulation step (2)). In the case where the ionizing radiation source 10 is used, a dose thereof can be controlled independently from the generation of a potential difference between the spinning nozzle 2 and the counter electrode 5; accordingly, the inorganic fiber aggregate can be stably obtained.

As the ionizing radiation source 10, various ionizing radiation sources can be used. In particular, an X-ray irradiation apparatus is desirable. There may be a potential difference between the counter electrode 5 and the spinning nozzle 2. The counter electrode 5 may be grounded or may be provided with a voltage. Furthermore, the ionizing radiation source 10 may be able to irradiate the fibers with radiation and is not necessary to be located behind the counter electrode 5. Still furthermore, the counter electrode 5 is not necessary to be formed into net-shape. As long as the ionizing radiation is allowed to go through, various members can be used, and even a vapor-deposited metal film may be used as the counter electrode.

Figure 6:
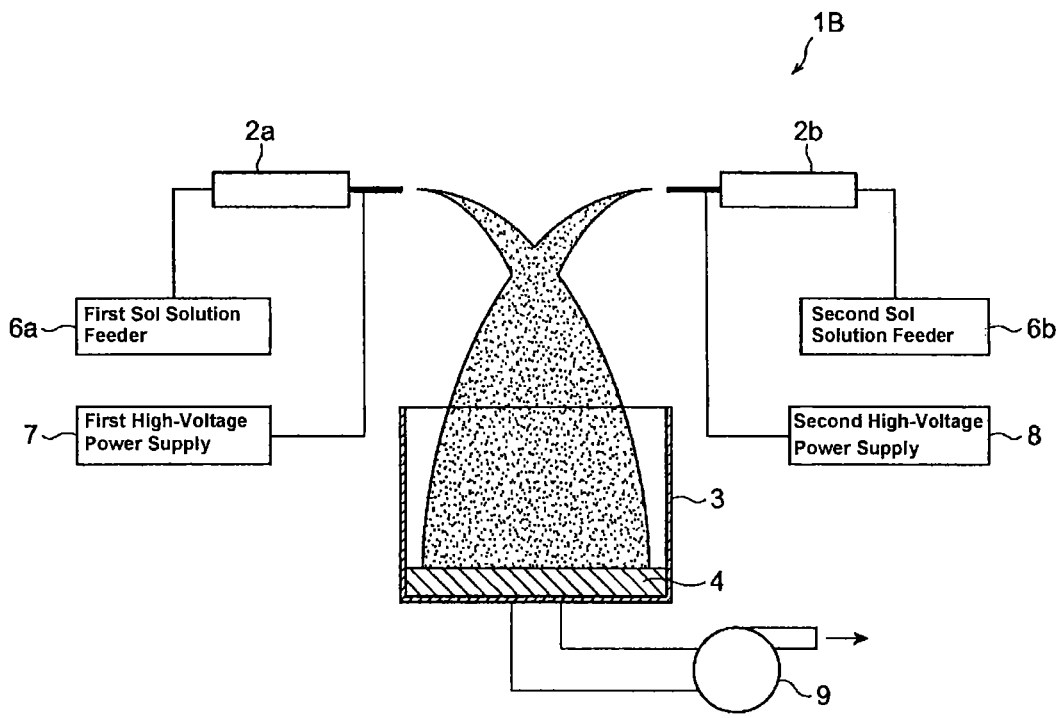
FIG. 6 is a schematic illustration illustrating still another embodiment of an electrospinning apparatus that can conduct a spinning step (1) and an accumulation step (2) in the producing method of the present invention.

FIG. 6 is a schematic illustration illustrating still another embodiment of an electrospinning apparatus that can conduct a spinning step (1) and an accumulation step (2) in the producing method of the present invention.

In FIG. 6, an electrospinning apparatus 1B has a first spinning nozzle 2a and a second spinning nozzle 2b, which are disposed facing with each other. To the first spinning nozzle 2a, a first sol solution feeder 6a that feeds the spinning inorganic sol solution and the first high voltage power supply 7 that applies a high voltage are connected, and, to the second spinning nozzle 2b, a second sol solution feeder 6b that feeds the spinning inorganic sol solution and the second high voltage power supply 8 that applies a high voltage having a polarity opposite to that of the first high voltage power supply 7, respectively, are connected. Others than what was mentioned above are constituted in a manner similar to the electrospinning apparatus 1, and duplicated explanations thereof will be omitted.

In the electrospinning apparatus 1B, while applying voltages having polarities opposite to each other to the first spinning nozzle 2a and the second spinning nozzle 2b from the first high voltage supply source 7 and second high voltage supply source 8, respectively, the spinning inorganic sol solution is discharged from the first spinning nozzle 2a and second spinning nozzle 2b (spinning step (1)). Then, fibers charged with polarities opposite to each other are oppositely discharged to come into contact and come near to neutralize charges, a flying force owing to an electrostatic force is lost, thereby the fibers fall by gravity or light wind and are recovered in a fiber collecting box 3. Accordingly, a low density and down-like inorganic fiber aggregate can be obtained (accumulation step (2)). When a sol solution discharge condition from the first spinning nozzle 2a and a sol solution discharge condition from the second spinning nozzle 2b are controlled to be different from each other, an inorganic fiber aggregate where different kinds of inorganic fibers are mingled, for example, being different in a fiber diameter, being different in a composition of fiber constituent, and the like, can be produced.

The spinning inorganic sol solution can be discharged continuously or discontinuously from the first spinning nozzle 2a and the second spinning nozzle 2b. Furthermore, an electric field may be generated between the first spinning nozzle 2a and the second spinning nozzle 2b, that is, a high voltage is applied only to either one thereof, and the other may be grounded. The first spinning nozzle 2a and the second spinning nozzle 2b may be heated or may not be heated.

In the electrospinning apparatus 1, electrospinning apparatus 1A, and electrospinning apparatus 1B, one spinning nozzle is used to each one spinning nozzle of 2, 2a and 2b. However, there is no need to use only one spinning nozzle. In some cases, in order to improve the productivity, two or more spinning nozzles may be provided.

Furthermore, in these electrospinning apparatuses, a suction machine 9 is disposed on the lower side of the collector 4 so that an air velocity in a spinning space may be set to 5 to 100 cm/second and preferably to 10 to 50 cm/second. However, in addition to the suction machine 9, or, in place thereof, an air blower may be disposed on the upper side of the collector 4. Thereby, collectivity of the fibers can be improved, and the inorganic fiber aggregates can be stably produced.

The inorganic fiber aggregate obtained according to the accumulation step (2) allows to conduct the following adhering step (3) to the accumulated inorganic fiber aggregate as it is, or, after the heat treatment, allows to conduct the following adhering step (3). When the heat treatment (hereinafter, if required to differentiate from an adhering heat treatment described below, in some cases, referred to as post-accumulation heat treatment) is conducted, a structure and a heat resistance of the inorganic fiber aggregate are stabilized.

The heat treatment can be conducted in an oven, a sintering furnace or the like. A temperature thereof is appropriately set depending on an inorganic component constituting the inorganic fiber aggregate.

The post-accumulation heat treatment temperature is preferably 200° C. or more, and more preferably 300° C. or more. When the heat treatment is conducted at such a temperature, a structure of the inorganic fiber aggregate is stabilized and the mechanical strength thereof is increased, that is, the fibers adhere to each other at intersections thereof; accordingly, during the following adhering step or the like, a shape of the inorganic fiber structure can be maintained.

On the other hand, when the post-accumulation heat treatment temperature is 500° C. or less, the hydrophilicity of the inorganic fiber structure can be increased. In addition, when the inorganic fiber structure is used as a culture substrate, cells can be readily cultured in spheroid form. For example, in the case where the inorganic fiber has hydroxyl groups, when the post-accumulation heat treatment is conducted at a temperature of 500° C. or less, an amount of hydroxyl groups per unit weight of fiber can be made 50 μmol/g or more; accordingly, the hydrophilicity is improved.

From the other point of view, when the post-accumulation heat treatment temperature is raised higher than 500° C., the hydrophobicity is increased and adhesiveness of cells can be increased; accordingly, when the inorganic fiber structure is used as a culture substrate, cells can be readily cultured in sheet form. Furthermore, since the adhesiveness between inorganic fibers is increased, the mechanical strength of the inorganic fiber structure can be increased.

In the adhering step (3), to an entirety including the inside of the inorganic fiber structure obtained by the previous steps, an adhering inorganic sol solution containing a compound mainly composed of inorganic components is imparted, an excess adhering inorganic sol solution is removed by gas-through, thereby an inorganic fiber aggregate containing the adhering inorganic sol solution was formed (hereinafter, in some cases, a first half step of the adhering step (3) is referred to as an adhering inorganic sol solution imparting step), followed by heat treating the inorganic fiber aggregate containing the adhering inorganic sol solution (or by naturally drying at room temperature), in an entirety including the inside, the inorganic fiber structure adhered with an inorganic adhesive is formed (hereinafter, in some cases, this second half step of the adhering step (3) is referred to as an adhering heat treatment step). If required to differentiate the heat treatment from the post-accumulation heat treatment, in some cases, the heat treatment in the adhering heat treatment step is referred to as an adhering heat treatment. As a raw material (compound) constituting the adhering inorganic sol solution, the raw material is the same as the compound containing elements constituting inorganic fibers. However, as long as the raw material permeates the inside of the inorganic fiber aggregate, the raw material may be the same as or different from the spinning inorganic sol solution. For example, there is no need of being spinnable, that is, the spinnability is not required. Furthermore, particles may be contained therein. The spinning inorganic sol solution may be diluted to use, that is, a concentration thereof can be appropriately selected. In particular, a condensate of metal alkoxide hydrolysate is preferred. Furthermore, the adhering inorganic sol solution may contain or may not contain a metal ion-containing compound which will be detailed in a step of imparting a solution containing a metal ion-containing compound (4).

When the adhering inorganic sol solution is imparted to an inorganic fiber aggregate, as long as the adhering inorganic sol solution can be reached the entirety uniformly, that is, reached the inside similarly with an exterior portion of the inorganic fiber aggregate, and imparted sufficiently, there is no particular restriction. For example, when the inorganic fiber aggregate is dipped in the adhering inorganic sol solution, the adhering inorganic sol solution can be imparted to the inorganic fiber aggregate. When the post-accumulation heat treatment of the inorganic fiber aggregate is conducted in the accumulation step (2), the inorganic fiber aggregate does not disperse even under the dip treatment.

An excess adhering inorganic sol solution contained in the inorganic fiber aggregate after dipping is removed by gas-through. The inorganic fiber aggregate is constituted of inorganic fibers; accordingly, when a gas is passed by suction or under pressure, a thickness is not collapsed, and, without forming a film between fibers of an entirety including the inside, an adhering inorganic sol solution containing inorganic fiber aggregate to which the adhering inorganic sol solution is imparted can be obtained.

In the adhering heat treatment step, the adhering inorganic sol solution containing inorganic fiber aggregate obtained in the adhering inorganic sol solution imparting step is dried, thereby, in an entirety including the inside, without forming a film between inorganic fibers, an inorganic fiber structure adhered with an inorganic adhesive can be produced. In the adhering heat treatment, a solvent or the like contained in the adhering inorganic sol solution may be volatilized. Without particularly restricting, the adhering heat treatment can be conducted by keeping, for example, at a temperature from 80 to 150° C. for 10 to 30 minutes. Also natural drying at room temperature may be conducted. The "adhering heat treatment" in the present description includes the following heat treatments in addition to the drying by heating and natural drying at room temperature.

In the adhering step (3), after the adhering heat treatment by which the solvent or the like is volatilized, as required, in order to mineralize the adhering inorganic sol solution and/or the inorganic fibers contained in the adhering inorganic sol solution containing inorganic fiber aggregate, a heat treatment can be conducted. When the heat treatment is conducted, the mechanical strength and heat resistance of the inorganic adhesive that bonded fiber intersections of the inorganic fiber aggregate are improved. Furthermore, the mechanical strength and heat resistance of the inorganic fiber are improved. The heat treatment can be conducted in, for example, a firing furnace, and the temperature is appropriately determined depending on the inorganic component constituting the inorganic adhesive and the inorganic fiber. In general, the heat temperature is preferred to be 200° C. or more, and more preferred to be 300° C. or more. Furthermore, when an inorganic fiber structure imparted with apatite and having functionality is produced, the heat treatment is preferably conducted at a heat temperature described below. According to the producing method of the present invention, the heat treatment like this may not be conducted.

When inorganic fibers are bonded with the inorganic adhesive without forming a film between inorganic fibers and without lowering the porosity, the heat treatment is preferably conducted under no load.

When the adhering heat treatment temperature is 500° C. or less, the hydrophilicity of the inorganic fiber structure can be increased. In addition, when the inorganic fiber structure is used as a culture substrate, cells can be readily cultured in spheroid form. For example, in the case where the inorganic fiber has hydroxyl groups, when the adhering heat treatment is conducted at a temperature of 500° C. or less, an amount of hydroxyl groups per unit weight of fiber can be made 50 µmol/g or more; accordingly, the hydrophilicity thereof is improved.

From the other point of view, when the adhering heat treatment temperature is set higher than 500° C., the hydrophobicity is increased and the adhesiveness of cells can be increased; accordingly, when the inorganic fiber structure is used as a culture substrate, cells can be cultured in a sheet form. Furthermore, since the adhesiveness between inorganic fibers is increased, the mechanical strength and the heat resistance of the inorganic fiber structure can be increased. The adhering heat treatment like this can be conducted in, for example, an oven, a sintering furnace or the like.

In a step where a solution containing a metal ion-containing compound is imparted (4), when a solution containing a metal ion-containing compound is imparted to the inorganic fiber structure, an inorganic fiber structure having functionality can be formed.

Examples of metals constituting the metal ion-containing compounds include calcium, sodium, iron, magnesium, potassium, copper, iodine, selenium, chromium, zinc, molybdenum, or the like. These metals work as a cell function inducing factor or exert an antibiotic action.

The metal ion-containing compound may be, for example, a metal salt. Examples of the metal salts include a chloride, a sulfate, a phosphate, a carbonate, a hydrogen phosphate, a hydrogen carbonate, a nitrate, a hydroxide and the like. In particular, a calcium ion containing salt-, a magnesium ion containing salt-, or an apatite-imparted inorganic fiber structure with functionality can conduct cell culture of which cell function is improved.

Examples of the method of imparting a metal ion-containing compound include a method where an inorganic fiber structure is dipped in a solution containing a metal ion-containing compound, a method where an inorganic fiber structure is coated or sprayed with a solution containing a metal ion-containing compound, and the like. When the inorganic fiber is a silica fiber, after the silica fibers are impregnated, coated or sprayed with the metal ion-containing compound, it is preferred to conduct the heat treatment to impart the metal ion-containing compound at a high concentration.

More specifically, an inorganic fiber structure having the functionality, to which a calcium ion containing salt or a magnesium ion containing salt is imparted, can be obtained by dipping the inorganic fiber structure in a solution in which, for example, a calcium salt or a magnesium salt is dissolved in an appropriate solvent (for example, lower alcohols), or by coating or spraying the inorganic fiber structure with the solution.

Furthermore, an inorganic fiber structure imparted with apatite and having functionality can be obtained, for example, by dipping inorganic fibers (in particular, silica fibers) containing hydroxyl groups on a surface thereof into a simulated body fluid containing at least phosphate ions and calcium ions to precipitate apatite on the inorganic fibers. In the case where the inorganic fiber is a silica fiber (in particular, in the case of a fiber structure for bone culture substrate), in the accumulation step (2), the post-accumulation heat treatment may be conducted or may not be conducted. However, when the post-accumulation heat treatment is conducted, the inorganic fiber aggregate is preferably heat treated at a temperature of 500° C. or less, and more preferably at a temperature of from 120° C. to 300° C. Like this, the post-accumulation heat treatment is not conducted, or, if conducted, at a temperature of 500° C. or less. Thereby, an amount of hydroxyl groups per unit weight of fiber can be made 50 µmol/g or more, and preferably 100 µmol/g or more.

Furthermore, after the adhering inorganic sol solution is imparted, in the adhering step (3), by conducting an adhering heat treatment (drying and/or heating) in a similar range of the temperature range, an amount of hydroxyl groups per unit weight of fiber is preferably made 50 µmol/g or more (more preferably 100 µmol/g or more).

An inorganic fiber structure of the present invention is an inorganic fiber structure where an inorganic fiber aggregate produced by at least a step where the inorganic fiber spun by an electrospinning method is irradiated with ions having a polarity opposite to that of the inorganic fiber to accumulate is adhered with an inorganic adhesive in an entirety including the inside. If desired, a metal ion-containing compound is imparted. The inorganic fiber structure of the present invention can be prepared according to, for example, a producing method of the present invention.

The inorganic fiber in the present invention includes, for example, an inorganic gel fiber, an inorganic dry gel fiber, or a sintered inorganic fiber.

The inorganic gel fiber is a fiber in a state containing a solvent. For example, when a raw material of an inorganic fiber is composed of tetraethoxysilane (TEOS), ethanol, water, and hydrochloric acid, a substance having the highest boiling point is water; accordingly, the inorganic gel fiber is a fiber heat treated at a temperature of less than 100° C. or not heat treated.

Furthermore, the inorganic dry gel fiber means a state where a solvent or the like contained in the gel fiber is come off. For example, when a raw material of an inorganic fiber is composed of tetraethoxysilane (TEOS), ethanol, water and hydrochloric acid, a substance having the highest boiling point is water; accordingly, the inorganic gel dry fiber is a fiber heat treated at a temperature of 100° C. or more.

Furthermore, the sintered inorganic fiber means a state where the inorganic dry gel fiber (porous) is sintered (nonporous). For example, in the case where a raw material of the inorganic fiber is a silica compound, the sintered inorganic fiber is a fiber treated with heat at 800° C. or more.

In the inorganic fiber structure of the present invention, an average fiber diameter of the inorganic nanofibers is 3 µm or less so that a surface area may be large and the functionality may be excellent. The average fiber diameter is preferably 2 µm or less and more preferably 1 µm or less.

"An average fiber diameter" means an arithmetic average value of fiber diameters at 50 points, and "a fiber diameter" means a line thickness of a fiber measured based on an electron microgram taken at 5000-fold magnification of an inorganic fiber structure.

Examples of a form of the inorganic fiber structure include a two-dimensional form like a nonwoven fabric; a three-dimensional form such as a hollow cylinder, and a cylinder; and the like. A three-dimensionally formed inorganic fiber structure can be produced, for example, by molding a two-dimensionally-formed inorganic fiber structure like a nonwoven fabric and the like.

The inorganic fiber structure of the present invention has the porosity (bulkiness) such high as 90% or more to be low in fiber density. Accordingly, the inside of the inorganic fiber structure can be efficiently utilized. For example, when the inorganic fiber structure is used as a culture substrate, since the fiber density is low, an advantage that cells can readily spread into the inside of the culture carrier is exerted. The porosity is preferably 91% or more, more preferably 92% or more, still more preferably 93% or more, and still more preferably 94% or more. The upper limit thereof is, though not particularly limited, preferably 99.9% or less because of excellent form stability.

The porosity can be calculated from the following formula.

$$P = [1 - Wf/(V \times SG)] \times 100$$

Herein, P, Wf, V, and SG, respectively represent porosity (%), a fiber weight (g), a volume (cm$^3$), and a specific gravity (g/cm$^3$) of fiber.

For example, when a thickness is uniform like a nonwoven fabric, the porosity can be calculated from the following formula.

$$P = \{1 - Wn/(t \times SG)\} \times 100$$

Herein, P, Wn, t, and SG, respectively represent porosity (%), a basis weight (g/m$^2$), a thickness (μm), and a specific gravity (g/cm$^3$) of fiber.

The basis weight is a value obtained by measuring an area of a plane having the largest area and a weight, followed by calculating a weight per 1 m$^2$, and a thickness is a value measured by a micrometer method by setting a load at 100 g/cm$^2$ in a plane having the largest area.

When the inorganic fiber structure has a two-dimensional form (in particular, nonwoven fabric), in order to secure the excellent shape-retaining property and the sufficient mechanical strength, the tensile rupture strength is preferably 0.2 MPa or more. The tensile rupture strength is preferably 0.3 MPa or more, more preferably 0.4 MPa or more, still more preferably 0.5 MPa or more, and still more preferably 0.55 MPa or more.

The tensile rupture strength is a quotient obtained by dividing a breaking load by a cross section area of the inorganic fiber structure. The breaking load is a value measured under the following condition, and a cross section area is a value obtained from a product of a width and a thickness of a test piece at the time of measurement.

Product name: Small tensile tester
Type: TSM-01-cre manufactured by Search Co., Ltd.
Test size: 5 mm (width)×40 mm (length)
Distance between chucks: 20 mm
Tensile speed: 20 mm/min.
Initial load: 50 mg/1 d An amount of hydroxyl groups per unit weight of fiber is, so as to be excellent in the hydrophilicity, preferably 50 μmol/g or more, more preferably 100 μmol/g or more, still more preferably 200 μmol/g or more, still more preferably 300 μmol/g or more, still more preferably 400 μmol/g or more, and still more preferably 500 μmol/g or more.

The amount of hydroxyl groups per unit weight of fiber is a quotient obtained by dividing an amount of hydroxyl groups of an inorganic fiber structure by an amount of fibers (unit: g) of the inorganic fiber structure used in the measurement of the amount of hydroxyl groups.

The amount of hydroxyl groups is a value measured by a neutralization titration method. That is, after the inorganic fiber structure is dispersed in a 50 ml of a 20 vol % sodium chloride aqueous solution, a 0.1 N sodium hydroxide aqueous solution is dropped up to a neutralization point. From a dropping amount of sodium hydroxide necessary to neutralize, an amount of hydroxyl groups of the inorganic fiber structure is determined (see, reference literatures).

REFERENCE LITERATURES

George W S., Determination of Specific Surface Area of Colloidal Silica by Titration with Sodium Hydroxide, Anal. Cheam.; 28, 1981-1983, (1956)

The inorganic fiber structure of the present invention is adhered with an inorganic adhesive in an entirety including the inside thereof without forming a film between the inorganic fibers; accordingly, the porosity of 90% or more can be retained. For example, when the inorganic fiber structure is used as a culture carrier, a feed efficiency of a nutrient and oxygen indispensable for cells can be improved, and, since a scaffold necessary for cell culture is abundant, high density culture can be attained.

An inorganic fiber structure with the functionality of the present invention can be obtained by imparting a metal ion-containing compound to an inorganic fiber structure having the porosity of 90% or more as mentioned above.

Examples of a metal constituting the metal ion-containing compounds include calcium, sodium, iron, magnesium, potassium, copper, iodine, selenium, chromium, zinc, molybdenum, and the like. These metals work as a cell function inducing factor or exert an antibiotic action.

The metal ion-containing compound may be, for example, a metal salt. Examples of a metal salt include a chloride, a sulfate, a phosphate, a carbonate, a hydrogen phosphate, a hydrogen carbonate, a nitrate, a hydroxide, and the like. In particular, a calcium ion containing salt-, a magnesium ion containing salt-, or an apatite-imparted inorganic fiber structure with the functionality can conduct cell culture of which cell function is improved.

EXAMPLES

The present invention now will be further illustrated by, but is by no means limited to, the following Examples.
<<Preparation and Evaluation of Inorganic Fiber Structure (Nonwoven Fabric)>>
(1) Preparation of Silica Fiber Nonwoven Fabric In the present example, 16 kinds of silica fiber nonwoven fabrics (Examples 1 to 9, and Comparative Examples 1 to 7) described in Table 1 were prepared and evaluated.
Spinning Step (1) and Accumulation Step (2)

Tetraethoxysilane as a metal compound, ethanol as a solvent, water for hydrolysis, and 1N hydrochloric acid as a catalyst were mixed at a molar ratio of 1:5:2:0.003, refluxed at a temperature of 78° C. for 10 hr, followed by removing a solvent by a rotary evaporator to concentrate, further followed by heating at a temperature of 60° C., thereby a sol solution having the viscosity of 2 poises was formed. By use of the resulted sol solution as a spinning solution (spinning inorganic sol solution), according to a neutralization spinning method (except for Comparative Examples 6 and 7) or a plate spinning method that is an electrospinning method (Comparative Examples 6 and 7), gel silica fiber webs were prepared.

The neutralization spinning method was conducted under the spinning condition the same as that of Example 8 of Japanese Unexamined Patent Publication (kokai) No. 2005-264374. That is, as the counter electrode 5 in FIG. 1, the counter electrode (creeping discharge element 25) in FIG. 4 was used. Hereinafter, details thereof will be described.

Spinning nozzle: metal syringe needle having an inner diameter of 0.4 mm (cut at the tip)

Distance between a spinning nozzle and a counter electrode: 200 mm

Counter electrode serving as ion generating electrode: A creeping discharge element in which, on a stainless plate (inductive electrode), an alumina film (dielectric substrate) having a thickness of 1 mm was thermally sprayed, thereon tungsten wires (discharge electrode) having a diameter of 30 μm were set at an equidistance of 10 mm (a tungsten wire plane was opposed to a spinning nozzle and grounded, an AC high voltage was applied at 50 Hz between the stainless plate and the tungsten wires by an AC high voltage power supply.)

First high voltage power supply: −16 kV
Second high voltage power supply: ±5 kV (peak voltage of an AC creepage: 5 kV, 50 Hz)
Air flow: horizontal direction 25 cm/sec, vertical direction 15 cm/sec
Atmosphere in a spinning chamber: temperature 25° C., humidity 40% RH or less
Continuous spinning time period: 30 min. or more Furthermore, the plate spinning method was conducted according to the following procedure. As a spinning apparatus, an apparatus illustrated in FIG. 1 of publication of Japanese Unexamined Patent Publication (kokai) No. 2005-194675 was used. A spinning solution was fed to a stainless nozzle having an inner diameter of 0.4 mm at 1 g/hr from a pump, while discharging the spinning solution to a spinning space (temperature 26° C., relative humidity 40% or less) from the nozzle, a voltage (−16 kV) was applied to the nozzle, a stainless non-porous roll (distance from the nozzle: 10 cm) that is a collector was grounded, an electric field was applied to the spinning solution to form silica gel fibers having a fine diameter and accumulated on a rotating non-porous roll, thereby a gel silica fiber web was formed.

Post-Accumulation Heat Treatment Step (3)

In the next place, the gel silica fiber webs obtained in the foregoing step, except for Example 7 and Comparative Example 1, were subjected to the post-accumulation heat treatment at heat treatment temperatures (120° C., 300° C., 500° C., or 800° C.) described in the column of step (3) of Table 1, thereby silica fiber webs (basis weight: 10 g/m$^2$) were prepared.

Adhering Inorganic Sol Solution Imparting Step (4)

As an adhering inorganic sol solution used for adhering between fibers, tetraethoxysilane as a metal compound, ethanol as a solvent, water for hydrolysis, and nitric acid as a catalyst were mixed at a molar ratio of 1:7.2:7:0.0039, and allowed to react at a temperature of 25° C., under stirring condition of 300 rpm for 15 hr. After the reaction, ethanol was used to dilute so that a solid concentration of silicon oxide may be 0.25%, thereby a silica sol dilute solution (adhering inorganic sol solution) was prepared.

Among the silica fiber webs obtained according to the foregoing step, the silica fiber webs of Examples 1 to 9 and Comparative Example 7 were dipped in the silica sol dilute solution, followed by removing the excess silica sol dilute solution by suction (a method A described in the column of step (4) of Table 1), thereby silica sol dilute solution containing silica fiber webs were prepared.

On the other hand, silica fiber webs of Comparative Examples 1 to 3 and 6, the present step was not conducted. As to Comparative Example 4, the silica sol dilute solution was sprayed to the silica fiber web obtained according to the foregoing step (a method B described in a column of step (4) of Table 1), thereby silica sol dilute solution containing silica fiber web was prepared. In the silica sol dilute solution containing silica fiber web, the silica sol dilute solution was imparted only onto a surface of the silica fiber web. As to Comparative Example 5, after the silica fiber web obtained according to the foregoing step was dipped in the silica sol dilute solution, a two roller press machine was used to remove an excess silica sol dilute solution (a method C described in a column of step (4) of Table 1), thereby a silica sol dilute solution containing silica fiber web was prepared.

Adhering Heat Treatment Step (5)

As to Examples 1 to 9, and Comparative Example 7, in order to remove by drying a solvent contained in the inorganic adhesive (silica sol dilute solution), the silica sol dilute solution containing silica fiber webs were kept in an atmosphere at 110° C. for 30 min. (adhering first heat treatment step). On the other hand, as to Comparative Examples 1 to 6, the adhering first heat treatment step was not conducted.

Subsequently, as to Example 2, Example 3, Example 5, Example 6, Comparative Example 4, Comparative Example 5, and Comparative Example 7, the silica sol dilute solution containing silica fiber webs obtained according to the foregoing step were subjected to the adhering heat treatment at a temperature (200° C. or 500° C.) described in a column of step (5) of Table 1 (adhering second heat treatment step), thereby silica fiber nonwoven fabrics were prepared.

On the other hand, as to Example 1, Example 4, Examples 7 to 9, Comparative Examples 1 to 3, and Comparative Example 6, the adhering second heat treatment step was not conducted.

(2) Evaluation of Silica Fiber Nonwoven Fabric

Each of 16 kinds of silica fiber nonwoven fabrics (Examples (Ex.) 1 to 9, and Comparative Examples (Comp.) 1 to 7) prepared in the foregoing (1) was cut into a size of 10 cm×10 cm, followed by conducting various kinds of measurements. Results are illustrated in Table 1. In all of the silica fiber nonwoven fabrics, an average fiber diameter of nanofibers constituting the silica fiber nonwoven fabric was 0.8 μm.

A thickness of a nonwoven fabric means a value measured by a micrometer method when a load is set at 100 g/cm$^2$, and an apparent density means a value obtained by dividing a basis weight (a weight in terms of 1 m$^2$) by a thickness.

Furthermore, conditions of breaking load measurement are shown below.
Product name: Small tensile tester
Type: TSM-01-cre manufactured by Search Co., Ltd.
Test size: 5 mm×40 mm
Distance between chucks: 20 mm
Tensile speed: 20 mm/min.
Initial load: 50 mg/1 d
The porosity was calculated from the following formula:

[Porosity(%)]=[1−(basis weight/thickness/specific gravity)]×100

(unit of basis weight=g/m$^2$, unit of thickness=μm, and specific gravity of silica=2 g/cm$^3$)

TABLE 1

|  | (3) [a] (° C.) | (4) [b] | (5) [c] First | (5) [c] Second | [d] (μm) | [e] (g/cm$^3$) | [f] (%) | [g] (MPa) | [h] |
|---|---|---|---|---|---|---|---|---|---|
| Comp. 1 | untreated | untreated | untreated | untreated | 94.2 | 0.111 | 94.4 | 0.029 | N |
| Comp. 2 | 500° C. | untreated | untreated | untreated | 94.2 | 0.107 | 94.6 | 0.039 |  |
| Comp. 3 | 800° C. | untreated | untreated | untreated | 93.0 | 0.115 | 94.2 | 0.040 |  |
| Ex. 7 | untreated | method A | 110° C. | untreated | 92.5 | 0.112 | 94.4 | 0.299 |  |
| Ex. 8 | 120° C. | method A | 110° C. | untreated | 91.8 | 0.114 | 94.3 | 0.295 |  |
| Ex. 9 | 300° C. | method A | 110° C. | untreated | 95.2 | 0.107 | 94.6 | 0.287 |  |
| Ex. 1 | 500° C. | method A | 110° C. | untreated | 92.9 | 0.110 | 94.5 | 0.283 |  |

TABLE 1-continued

| | (3) [a] (°C.) | (4) [b] | (5) [c] First | (5) [c] Second | [d] (μm) | [e] (g/cm³) | [f] (%) | [g] (MPa) | [h] |
|---|---|---|---|---|---|---|---|---|---|
| Ex. 2 | 500° C. | method A | 110° C. | 200° C. | 93.6 | 0.112 | 94.4 | 0.343 | |
| Ex. 3 | 500° C. | method A | 110° C. | 500° C. | 93.2 | 0.117 | 94.2 | 0.513 | |
| Ex. 4 | 800° C. | method A | 110° C. | untreated | 94.0 | 0.114 | 94.3 | 0.275 | |
| Ex. 5 | 800° C. | method A | 110° C. | 200° C. | 93.8 | 0.113 | 94.3 | 0.393 | |
| Ex. 6 | 800° C. | method A | 110° C. | 500° C. | 94.2 | 0.111 | 94.4 | 0.568 | |
| Comp. 4 | 800° C. | method B | untreated | 500° C. | 93.2 | 0.113 | 94.4 | 0.048 | |
| Comp. 5 | 800° C. | method C | untreated | 500° C. | 52.1 | 0.205 | 89.7 | 1.264 | |
| Comp. 6 | 800° C. | untreated | untreated | untreated | 46.1 | 0.221 | 88.8 | 0.718 | P |
| Comp. 7 | 800° C. | method A | 110° C. | 500° C. | 45.9 | 0.222 | 88.6 | 0.786 | |

[a]: Heat treatment temperature
[b]: Imparting method
[c]: Heat treatment temperature (° C.)
[d]: Thickness
[e]: Apparent density
[f]: Porosity
[g]: Tensile rupture strength
[h]: Spinning method
N: Neutralization spinning
P: Plate spinning Preparation of Culture Carrier Comparative Example 8

The gel silica fiber web obtained according to the Comparative Example 1 was used as a comparative culture carrier (hereinafter, referred to as culture carrier a) used in the following evaluation tests. An average fiber diameter of nanofibers constituting the culture carrier was 0.8 μm.

Comparative Example 9

The silica fiber web obtained according to the Comparative Example 3 was used as a comparative culture carrier (hereinafter, referred to as culture carrier b) used in the following evaluation tests. An average fiber diameter of nanofibers constituting the culture carrier was 0.8 μm.

Example 10

Tetraethoxysilane as a metal compound, ethanol as a solvent, water for hydrolysis, and nitric acid as a catalyst were mixed at a molar ratio of 1:7.2:7:0.0039, allowed to react at a temperature of 25° C. for 15 hr under stirring condition of 300 rpm, followed by diluting with ethanol so that a solid concentration of silicon oxide may be 0.5%, thereby a silica sol dilute solution (adhering inorganic sol solution) was prepared.

After the silica fiber web obtained according to the Comparative Example 3 was dipped in the silica sol dilute solution, an excess sol solution was removed by suction, thereby a silica sol dilute solution containing silica fiber web was prepared.

In order to remove by drying a solvent contained in the silica sol dilute solution, the silica sol dilute solution containing silica fiber web was kept in an atmosphere of 110° C. for 30 min. (adhering first heat treatment step).

Subsequently, the silica sol dilute solution containing silica fiber web was subjected to an adhering second heat treatment at a temperature of 500° C., thereby a silica fiber nonwoven fabric (porosity: 93%, tensile rupture strength: 0.572 MPa, and an amount of hydroxyl groups: 35 μmol/g) was produced. The silica fiber nonwoven fabric was used as a culture carrier (culture carrier A). An average fiber diameter of nanofibers constituting the culture carrier was 0.8 μm.

Comparative Example 10

PVA (polymerization degree: 1000, complete saponification type) was adjusted to a concentration of 15 wt % and used as a spinning solution.

As a spinning apparatus, an apparatus described in FIG. 1 of publication of Japanese Unexamined Patent Publication (kokai) No. 2005-194675 was used. The spinning solution prepared in advance was fed at 0.5 g/hr from a pump to a stainless nozzle having an inner diameter of 0.4 mm, while discharging the spinning solution into a spinning space (temperature 26° C., relative humidity 50%) from the nozzle, a voltage (24 kV) was applied to the nozzle and a stainless non-porous roll that is a collector (distance to the nozzle: 10 cm) was grounded to apply an electric field to the spinning solution to form PVA fibers having a fine diameter, the PVA fibers were accumulated on a rotating non-porous roll, thereby a PVA fiber web was formed.

The PVA fiber web was subjected to the post-accumulation heat treatment at 150° C. for 30 min. to insolubilize. The resulted PVA-electrospinning nonwoven fabric (porosity: 83%) was used as a culture carrier (culture carrier c). An average fiber diameter of nanofibers constituting the culture carrier was 0.2 μm.

<<Evaluation of Culture Carrier>>

(1) Evaluation with CHO-K1 Derived from Chinese Hamster Ovary Cells

In the culture of CHO-K1 cells (ATCC: CCL-61, reference literature: Puch T T, et al., Genetics of somatic mammalian cells III. Long-term cultivation of euploid cells from human and animal subjects., J. Exp. Med. 108:945-956, 4958. PudMed: 13598821), a medium where 10% FBS (fetal bovine serum), and antibacterial agents (60 μg/mL of penicillin and 100 μg/mL of streptomycin) were added to DMEM (Dulbecco's Modified Eagle's Medium) was used under the condition of 37° C., 5% $CO_2$.

As the culture environment, in each well of 24-well plate, an evaluation culture carrier (1 cm×1 cm) was placed, 1 mL of CHO-K1 cells (5×10⁵ cells/mL) was inoculated, and the medium was exchanged each day.

Figure 7:
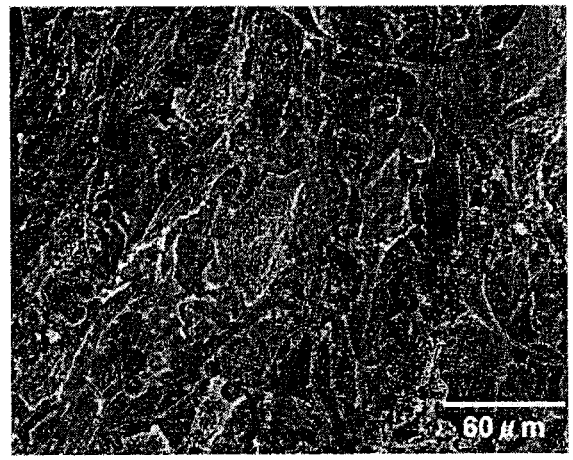
FIG. 7 is a SEM photograph illustrating a form of CHO-K1 cells cultured for 14 days on a culture carrier A of the present invention prepared according to example 10.
Figure 8:
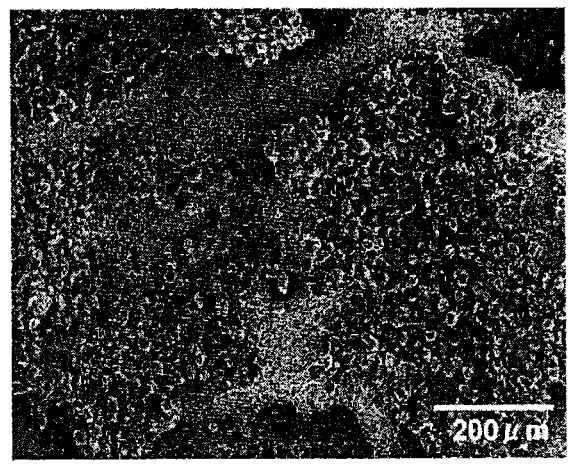
FIG. 8 is a SEM photograph illustrating a form of CHO-K1 cells cultured for 14 days on a comparative culture carrier c prepared according to comparative example 10.
Figure 9:
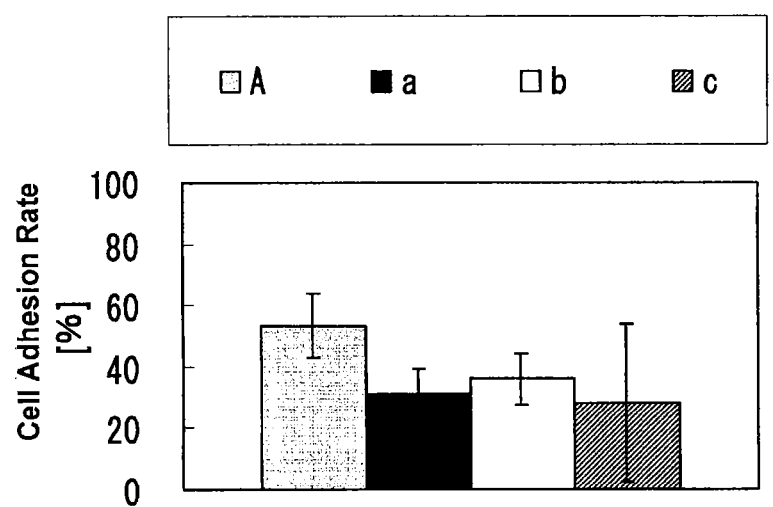
FIG. 9 is a graph illustrating cell adhering rates of CHO-K1 cells on a culture carrier A of the present invention prepared according to example 10 and on comparative culture carriers a to c prepared according to comparative examples 8 to 10.
Figure 10:
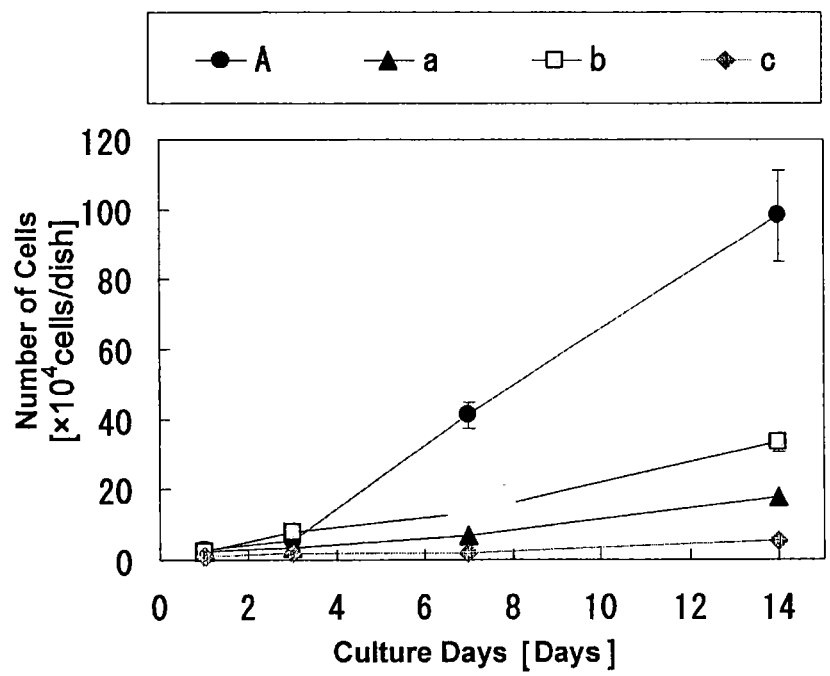
FIG. 10 is a graph illustrating a variation of the number of cells per unit dish of CHO-K1 cells up to 14 days of period of culture in the respective culture carriers shown in FIG. 9.

SEM photographs that show cell forms at the 14th day of the culture days of a culture carrier A of the present invention prepared according to the Example 10, and, comparative culture carriers a, b, and c prepared according to Comparative Examples 8 to 10 are illustrated in FIG. 7 (culture carrier A) and FIG. 8 (culture carrier c); cell adhesion rates as an index of cell adhesiveness at the first day of the culture days, in FIG. 9; and variations of the numbers of cells per unit dish up to the 14th day, in FIG. 10, respectively. The cell adhesive capacity was evaluated based on a cell adhesion rate calculated from a formula:

(number of cells on a carrier/number of inoculated cells)×100.

While, in the culture carrier A of the present invention, as illustrated in FIG. 7, the CHO-K1 cells adhered to and extended on an entire carrier surface and multiplied, in the comparative culture carrier c, cells multiplied with spherical cell blocks forming on a surface of the culture carrier.

When the cell adhesion capability was compared between the culture carrier A and the culture carriers a to c, it was found that, as illustrated in FIG. 9, the cell adhesion rate between the cells and the carrier of the culture carrier A was the highest, that is, cells excellently adhered on the fibers. A cell form of the cell carrier c is one of reasons why an interaction relating to adhesion between the carrier and the cells is weak.

As illustrated in FIG. 10, during the culture for two weeks, the culture carrier A of the present invention is remarkably improved in the cell proliferation capability than the culture carriers a to c. In the culture carriers a to b, when several days passed from the start of culture, the fibers loosened in a culture liquid, and the carrier expanded; accordingly, observation was difficult and operability was poor. Furthermore, the culture carrier c was such dense in structure as to be difficult to observe, and poor in the operability.

The culture carriers a to b prepared according to the neutralization spinning method, though sufficient in surface area that is a scaffold of cells necessary to conduct three-dimensional culture, lack in adhesion between fibers, or have a very weakly adhered structure; accordingly, the shape-retaining property in the culture liquid is poor. Accordingly, a uniform space that is a scaffold of cells can not be maintained, thereby excellent cell proliferation is difficult to occur. On the other hand, in the culture carrier A, a scaffold of cells necessary for cell proliferation is present sufficiently, fibers are bonded therebetween to be excellent in the shape-retaining property in the culture liquid, and the porosity of 90% or more and a uniform culture space can be maintained; accordingly, cell culture at high density is possible. In addition, a feed efficiency of a nutrient and oxygen indispensable for the cells can be improved; accordingly, excellent cell proliferation can be realized.

The control of the fiber density and the thickness in the cell culture carriers of the present invention has achieved an improvement in cell proliferation capability.

(2) Evaluation with Cell Strain HepG2 Derived from Human Liver Cancer

In the culture of HepG2 cells (ATCC:HB-0865, reference literature: Knowles B B, et al., Human hepatocellular carcinoma cell lines secrete the major plasma proteins and hepatitis B surface antigen., Science 209:497-499, 1980. PubMed: 6248960), a medium obtained by adding 10% fetal bovine serum (FBS), antibacterial agents (60 μg/mL of penicillin and 100 μg/mL of streptomycin), and 1 mmol/L of $NH_4Cl$ were added to William's Medium E (available from Sigma-Aldrich Corporation) was used under conditions of 37° C., 5% $CO_2$.

As the culture environment, in each well of 24-well plate, an evaluation culture carrier (1 cm×1 cm) was placed, 1 mL of HepG2 cells ($5\times10^5$ cells/mL) was inoculated, and the medium was exchanged every day.

Figure 11:
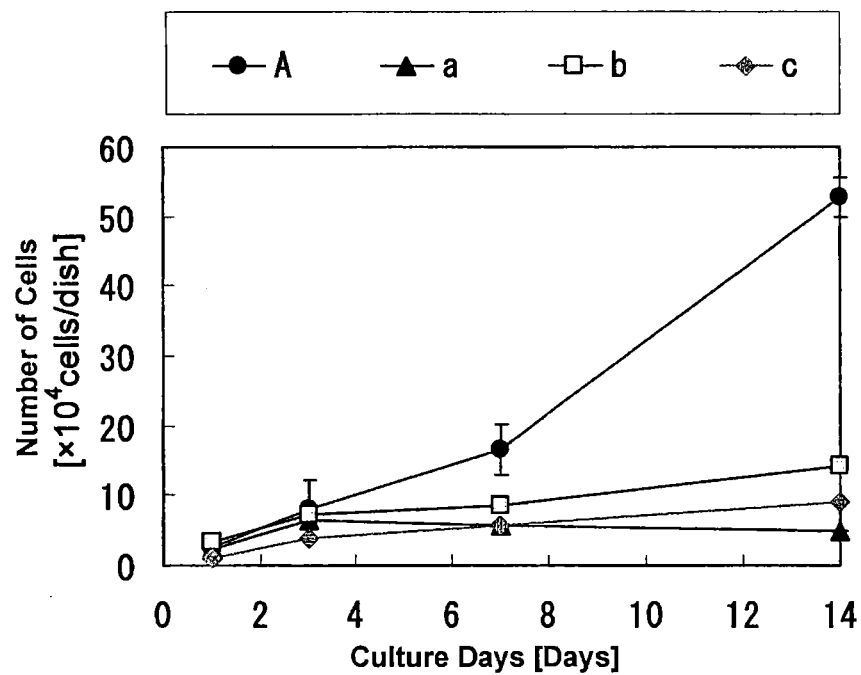
FIG. 11 is a graph illustrating a variation of the number of cells per unit dish of HepG2 cells up to 14 days of period of culture in a culture carrier A of the present invention prepared according to example 10 and comparative culture carriers a to c prepared according to comparative examples 8 to 10.
Figure 12:
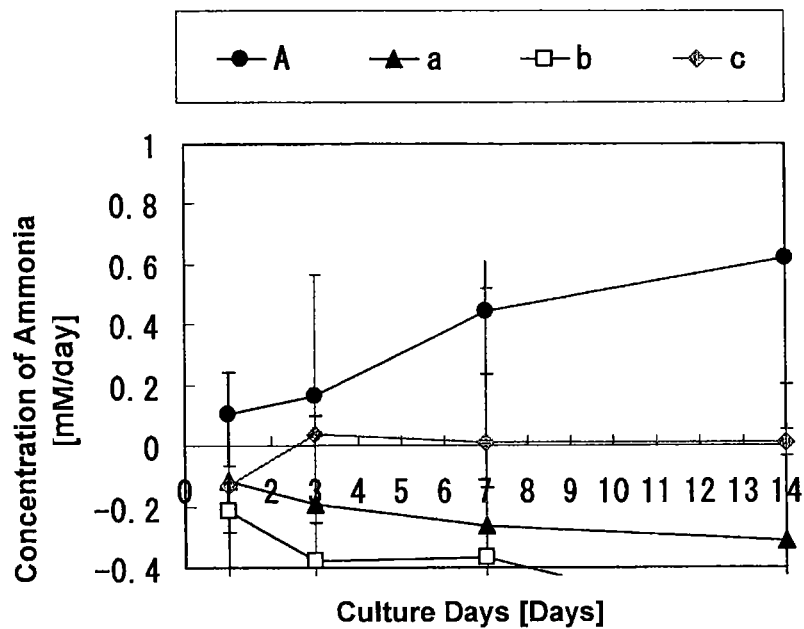
FIG. 12 is a graph illustrating measurement results of ammonia removal capability (variation of ammonia concentration per unit dish) in a medium, which is caused by HepG2 cells up to 14 days of period of culture in the respective culture carriers illustrated in FIG. 11.
Figure 13:
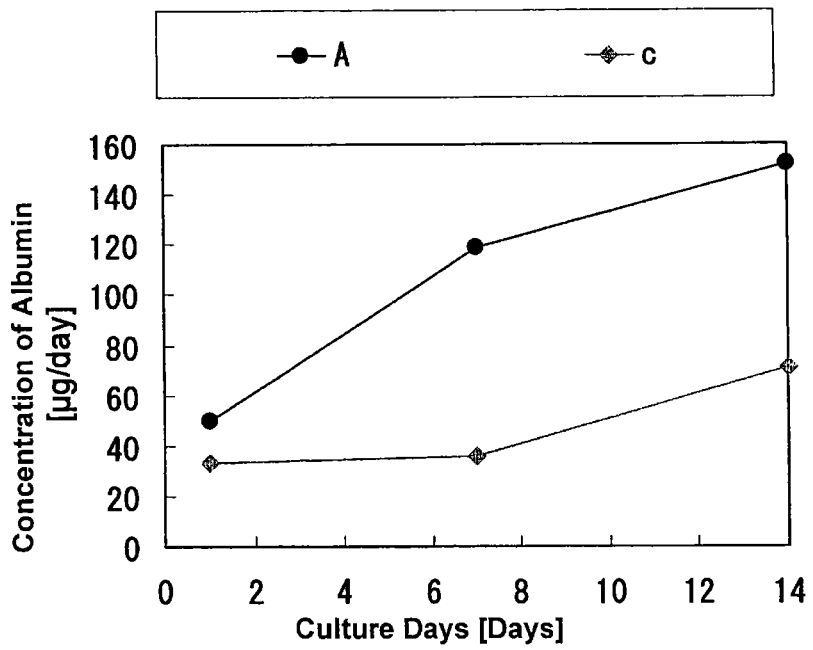
FIG. 13 is a graph illustrating measurement results of a variation of albumin concentration (per unit dish) of HepG2 cells up to 14 days of period of culture in the respective culture carriers illustrated in FIG. 11.

Of the culture carrier A of the present invention prepared according to the Example 10, and, comparative culture carriers a, b, and c prepared according to Comparative Examples 8 to 10, variations of the numbers of cells per unit dish up to 14 days are illustrated in FIG. 11; measurement results of ammonia removal capability in the medium which was caused by the cells up to 14 days, in FIG. 12; and variations of the albumin concentration of the cells up to 14 days, in FIG. 13, respectively.

As illustrated in FIG. 11, when HepG2 was cultured on the culture carrier A of the present invention and the comparative culture carriers a to c for 14 days, the culture carrier A was remarkably improved in the cell proliferation capability than the culture carriers a to c.

When the ammonia removal capability was compared, as illustrated in FIG. 12, during the culture period of two weeks, the culture carriers a to c did not exhibit an improvement in cell function, by contrast, ammonia was tend to be secreted. However, according to the culture carrier of the present invention, the cell function was improved, and detoxification capability (ammonia removal capability) that is one of functions intrinsic to the liver cells was improved.

The HepG2 cells, in a single layer culture (two-dimensional culture on a dish), secrete ammonia. However, when the HepG2 cells are sterically cultured in three-dimension, a feature that an absorbing and metabolizing function of ammonia is generated is obtained. Accordingly, in the comparative cell culture carriers, an advantage due to three-dimensional cells is not exhibited. However, the culture carrier A of the present invention is three-dimensionally cultured, that is, in a state close to a state of liver cells in a living body.

When a variation of the albumin concentration of the HepG2 cells cultured on the culture carrier A is checked, as illustrated in FIG. 13, the albumin concentration increases during culture period; accordingly, the HepG2 cells cultured on the culture carrier A normally proliferate.

(3) Overall Evaluation

An overall evaluation based on results of the (1) and (2) are shown in Table 2.

A cell proliferation capability in Table 2 was evaluated based on Comparative Example 10 (Comp. 10) (PVA). As to the cell adhesiveness, roughly speaking, about 30% or less was evaluated as "+", about 30% to 50% was evaluated as "++", and about 50% or more was evaluated as "+++".

TABLE 2

|  | Ex. 10 | Comp. 8 | Comp. 9 | Comp. 10 |
| --- | --- | --- | --- | --- |
| Cell proliferation capability | +++ | + | ++ | ++ |
| Cell adhesivenes | +++ | ++ | ++ | + |
| Observability | +++ | ++ | ++ | + |
| Operability | +++ | + | ++ | + |

<<Preparation of Functional Inorganic Fiber Structure>>

Tetraethoxysilane as a metal compound, ethanol as a solvent, water for hydrolysis, and 1N hydrochloric acid as a catalyst were mixed at a molar ratio of 1:5:2:0.003, refluxed at a temperature of 78° C. for 10 hr, followed by removing a solvent by a rotary evaporator to concentrate, further followed by heating at a temperature of 60° C., thereby a sol solution having a viscosity of 2 poises was formed. By use of the resulted sol solution as a spinning liquid (spinning inorganic sol solution), according to a neutralization spinning method, that is, by spinning according to the electrospinning method and by irradiating with ions having an opposite polarity to accumulate, thereby a gel fiber web (inorganic fiber aggregate) was formed.

The neutralization spinning method was conducted under the same spinning condition as that in Example 8 of Japanese Unexamined Patent Publication (kokai) No. 2005-264374. That is, as the counter electrode 5 in FIG. 1, the counter electrode (creeping discharge element 25) in FIG. 4 was used. Hereinafter, details thereof will be described.

Spinning nozzle: metal syringe needle having an inner diameter of 0.4 mm (cut at the tip).

Distance between a spinning nozzle and a counter electrode: 200 mm

Counter electrode serving as ion generating electrode: A creeping discharge element in which, on a stainless plate (inductive electrode), an alumina film (dielectric substrate) having a thickness of 1 mm was thermally sprayed, thereon tungsten wires (discharge electrode) having a diameter of 30 μm were set at an equidistance of 10 mm (a tungsten wire plane was faced to a spinning nozzle and grounded, and an AC high voltage was applied at 50 Hz between the stainless plate and the tungsten wire by an AC high voltage power supply.)

First high voltage power supply: −16 kV

Second high voltage power supply: ±5 kV (peak voltage of an AC creepage: 5 kV, 50 Hz)

Air flow: horizontal direction 25 cm/sec, vertical direction 15 cm/sec

Atmosphere in a spinning chamber: temperature 25° C., humidity 40% RH or less

Continuous spinning time period: 30 min. or more

The resulted gel fiber webs (inorganic fiber aggregates) were subjected to the post-accumulation heat treatment at a temperature of 800° C., 120° C., or 500° C., thereby heated inorganic fiber aggregates (in sequence, "sample 1", "sample 2", and "sample 3") were formed.

Tetraethoxysilane as a metal compound, ethanol as a solvent, water for hydrolysis, and nitric acid as a catalyst were mixed at a molar ratio of 1:7.2:7:0.0039, allowed to react at a temperature of 25° C. for 15 hr under stirring condition of 300 rpm, followed by diluting with ethanol so that a solid concentration of silicon oxide may be 0.25%, thereby a silica sol dilute solution (adhering inorganic sol solution) was formed.

In the adhering inorganic sol solution (solid concentration: 0.25%), the samples 1 to 3, respectively, were dipped, followed by removing the excess silica sol dilute solution by suction, further followed by holding in an atmosphere of 110° C. for 30 min. to remove a solvent of the silica sol dilute solution, thereby, an adhered sample 1, an adhered sample 2, and an adhered sample 3 were respectively formed (adhering first heat treatment).

A heated adhering sample 1 obtained by subjecting the adhering sample 1 to adhering second heat treatment at a temperature of 500° C. for 3 hr was rendered Example 14 (porosity: 94.3%, tensile rupture strength: 0.568 MPa, amount of hydroxyl groups: 37 μmol/g). Furthermore, the adhering sample 2 was taken as Example 15 (porosity: 93.5%, tensile rupture strength: 0.292 MPa, and amount of hydroxyl groups: 1500 μmol/g).

Furthermore, a heated adhering sample 3 obtained by heating the adhering sample 3 at a temperature of 500° C. for 3 hr (porosity: 94.2%, tensile rupture strength: 0.513 MPa, amount of hydroxyl groups: 54 μmol/g) was dipped in a calcium chloride-ethanol solution (concentration: 0.1N) for 3 hr, followed by heating at 500° C. for 3 hr, further followed by washing with water, thereby a calcium containing fiber structure 1 was prepared, and this was rendered Example 11. By X-ray photoelectron spectroscopy, elements in the calcium containing fiber structure 1 were analyzed and it was found that an element ratio of calcium was 14.36%. For reference, a calcium element ratio of the heated adhering sample 3 (standard product) was 0.51%.

Furthermore, the heated adhering sample 3 obtained by heating the adhering sample 3 at 500° C. for 3 hr was dipped in a magnesium chloride-ethanol solution (concentration: 0.1N) for 3 hr, followed by heating at 500° C. for 3 hr, further followed by washing with water, thereby a magnesium containing fiber structure 2 was prepared, and this was taken as Example 12. When, by X-ray photoelectron spectroscopy, elements in the magnesium containing fiber structure 2 were analyzed, it was found that an element ratio of magnesium was 22.54%. For reference, an element ratio of magnesium of the heated adhering sample 3 (standard product) was 0.94%.

Furthermore, in a separately prepared simulated body liquid (a solution having ion concentrations the same as that of the human body fluid that contains 142.0 mmol/L of $Na^+$, 103.0 mmol/L of $Cl^-$, 10.0 mmol/L of $HCO_3^-$, 5.0 mmol/L of $K^+$, 1.5 mmol/L of $Mg_2^+$, 2.5 mmol/L of $Ca_2^-$, 1.0 mmol/L of $HPO_4^{2-}$, and 0.5 mmol/L of $SO_4^{2-}$), the adhering sample 2 (amount of hydroxyl groups: 1500 μmol/g) was dipped for one week to precipitate apatite on a fiber surface, thereby an apatite containing fiber structure 3 was prepared, and this was taken as Example 13.

<<Function Evaluation of Functional Inorganic Fiber Structure>>

Of Examples 11 to 15 described below, various function evaluations as a culture carrier were conducted. In all of the fiber structures, an average fiber diameter of nanofibers constituting the fiber structure was 0.8 μm.

(Example 11) Calcium containing fiber structure 1
(Example 12) Magnesium containing fiber structure 2
(Example 13) Apatite containing fiber structure 3
(Example 14) Heated adhering sample 1
(Example 15) Adhering sample 2

On the fiber structures or samples, respectively, human osteosarcoma MG63 cells (IFO50108) were cultured, and the differentiation capability to adult bone was compared and studied. As a medium, a medium obtained by adding 10% fetal bovine serum (FBS), an antibacterial agent, and 0.1% of non-essential amino acid to MEM medium (Invitrogen Corporation) was used. On the sample or fiber structure, 1 ml of $2 \times 10^5$ cells/mL was inoculated, followed by culturing for 21 days, further followed by evaluating.

Figure 14:
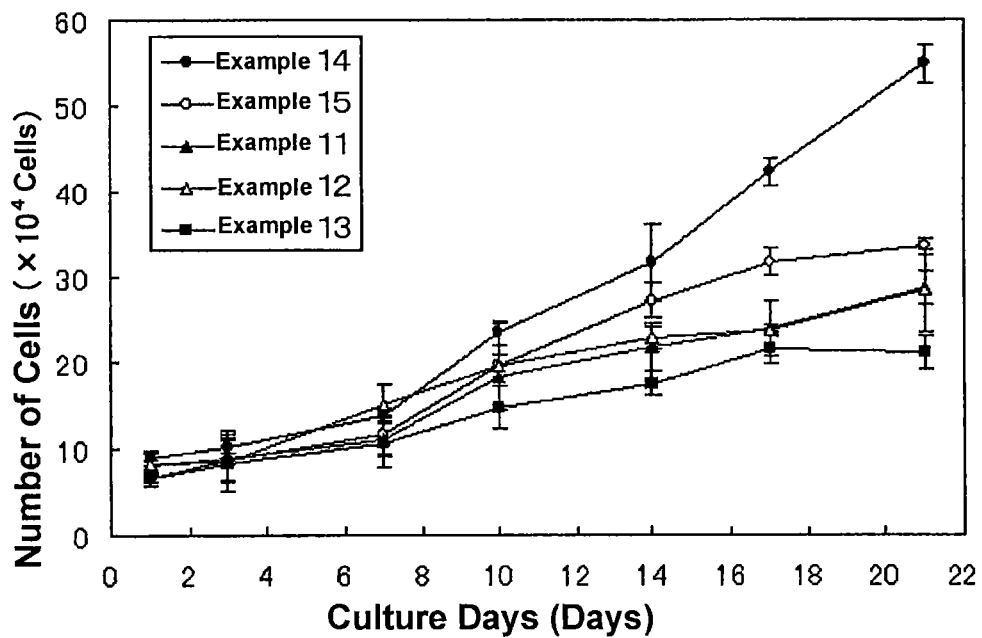
FIG. 14 is a graph illustrating a variation of the number of cells of human bone cancer MG63 cells cultured for 21 days on inorganic fiber structures of examples 11 to 13 that are preferable embodiments of the present invention and the respective samples of the examples 14 to 15 of the present invention.
Figure 15:
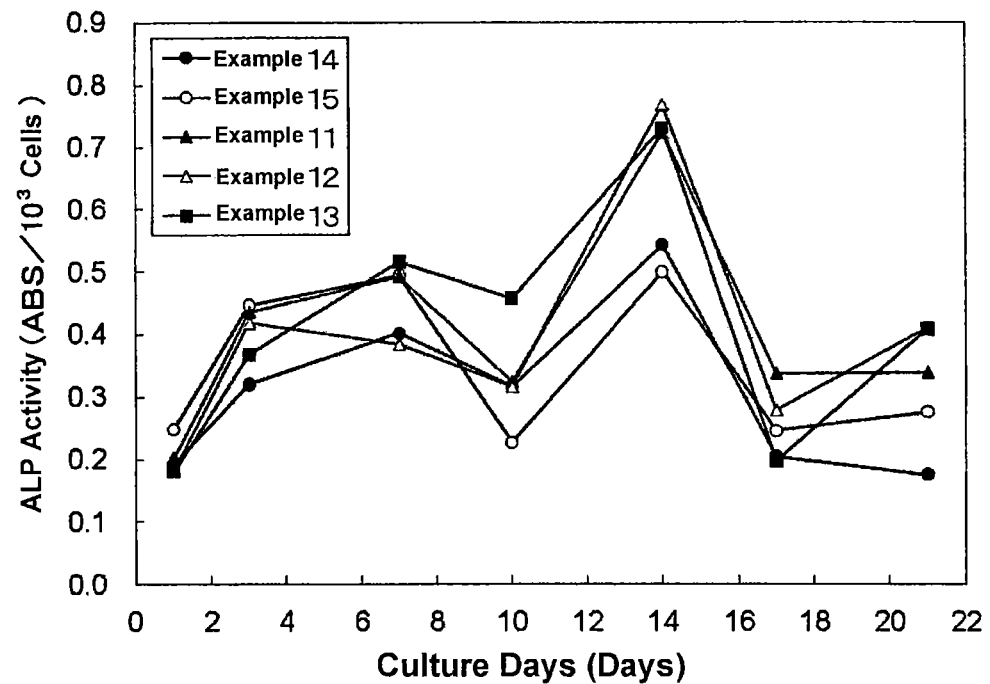
FIG. 15 is a graph illustrating a variation with time of enzyme activity (unit: $ABS/10^3$ cells) per unit cell of alkali phosphatase (ALP) secreted from human bone cancer MG63 cells in a culture illustrated in FIG. 14.
Figure 16:
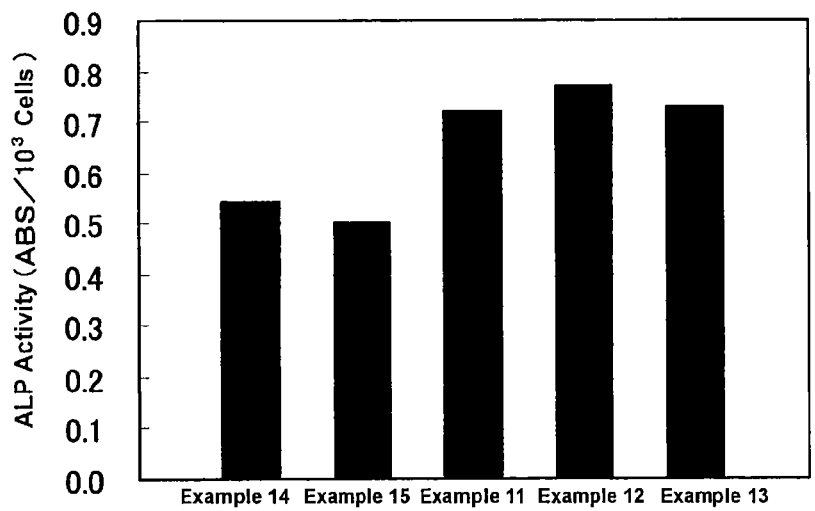
FIG. 16 is a graph illustrating values on the 14th day of culture period, relating to the ALP enzyme activity illustrated in FIG. 15.

A transition of the number of cells is illustrated in FIG. 14. Furthermore, a transition with time of the enzyme activity (unit: $ABS/10^3$ cell) per unit cell of alkali phosphatase (ALP) that is an enzyme secreted when bone cells are differentiated to bone is illustrated in FIG. 15, and values at the 14th day of the culture are illustrated in FIG. 16. The stronger the activity of ALP is, the easier the cell differentiation to bone is. The ALP activity was determined in such a manner that, after the respective fiber structures or samples were washed with a phosphoric acid buffer solution, 100 μL of 1% Triton X-100 containing phosphoric acid buffer solution was added, followed by shaking at 37° C. for 30 min., further followed by adding 100 μL of 0.006 g/mL p-nitro phenyl phosphate, further followed by shaking for 2 hr, further followed by measuring absorbance at a wavelength of 405 nm of a reaction liquid.

As illustrated in FIGS. 14 to 16, the fiber structures of the present invention, which do not contain a metal ion-containing compound (Examples 14 and 15) are excellent in the cell proliferation capability compared with the calcium containing fiber structure 1 (Example 11), the magnesium containing fiber structure 2 (Example 12), and the apatite containing fiber structure 3 (Example 13), which are the preferred embodiments of the present invention. However, cells low in cell function are cultured.

When compared with the ALP activities of the respective fiber structures at the 14th day of the culture each other, each of the fiber structures of Examples 11 to 13 is higher in the ALP activity than the fiber structure of Example 14 or 15. When Example 12 of which ALP activity value was the highest and Example 15 of which ALP activity value was the lowest are compared, there is a difference of 1.5 times, that is, the cells of Example 12 are cells that readily cause differentiation induction to bone.

Accordingly, the fiber structure having functionality, which is a preferable embodiment of the present invention, is effective when a cell culture of which cell function is increased is desired to conduct.

Reference Example

Measurement of Amounts of Hydroxyl Groups in Inorganic Fiber Structures Different in Heat Treatment Temperature, and Evaluation of Cell Culture (1) Preparation of Inorganic Fiber Structure and Measurement of Amount of Hydroxyl Groups The gel silica fiber webs (unheated) obtained according to the Comparative Example 1 were heated up to temperatures of 120° C., 200° C., 250° C., 300° C., 500° C. and 800° C. at a speed of 1° C./min. and held there for 3 hr to heat treat at the respective temperatures, followed by measuring amounts of hydroxyl groups per unit weight of fiber. Also in all of the silica fiber nonwoven fabrics, or, the gel silica fiber webs before heating, an average fiber diameter of nanofibers constituting the silica fiber nonwoven fabric or web was 0.8 µm.

Figure 17:
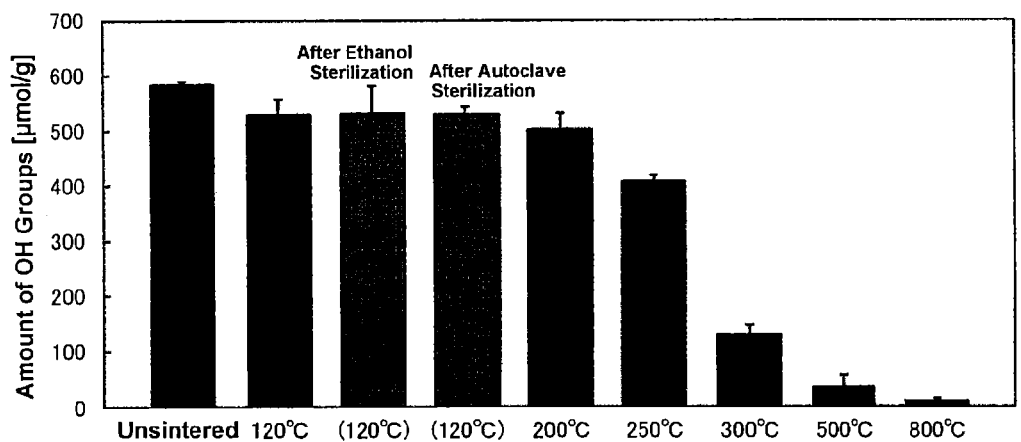
FIG. 17 is a graph illustrating a relationship between a heat treatment temperature and an amount of hydroxyl groups.

Results are illustrated in FIG. 17. In FIG. 17, by considering the case where the inorganic fiber structure is used as a cell culture carrier, after the inorganic fiber structure was heat treated at 120° C., ethanol sterilization or autoclave sterilization was conducted. Amounts of hydroxyl groups per unit weight of fiber after the sterilization are also exhibited.

From FIG. 17, it was found that when a temperature is 500° C. or less, an amount of hydroxyl groups per unit weight of fiber can be made 50 µmol/g or more, when a temperature is 300° C. or less, an amount of hydroxyl groups per unit weight of fiber can be made 100 µmol/g or more, when a temperature is 250° C. or less, an amount of hydroxyl groups per unit weight of fiber can be made 400 µmol/g or more, and when a temperature is 200° C. or less, an amount of hydroxyl groups per unit weight of fiber can be made 500 µmol/g or more.

Furthermore, it was also found that an amount of hydroxyl groups per unit weight of fiber after ethanol sterilization or autoclave sterilization is not different from that before sterilization.

(2) Preparation of Culture Carrier and Cell Culture Evaluation

The gel silica fiber webs (unheated) obtained according to the Comparative Example 1 were heated up to a temperature of 100° C., 300° C., or 500° C. at a speed of 1° C./min. and held at the temperatures for 3 hr. Thereby, culture carriers were prepared.

By use of these respective culture carriers (in addition, as a reference, gel silica fiber web before heating), under the culture conditions mentioned above, cell strains HepG2 derived from human liver cancer were cultured for 14 days.

Figure 18:
FIG. 18 is a SEM photograph illustrating a form of HepG2 cells cultured for 14 days on the culture carrier of Reference Example 1.
Figure 19:
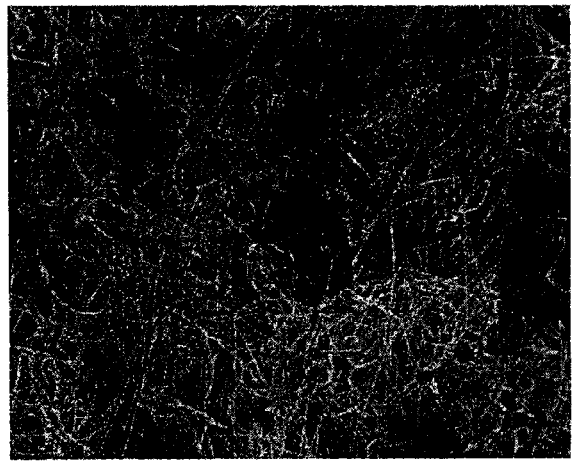
FIG. 19 is a SEM photograph illustrating a form of HepG2 cells cultured for 14 days on the culture carrier of Reference Example 2.
Figure 20:
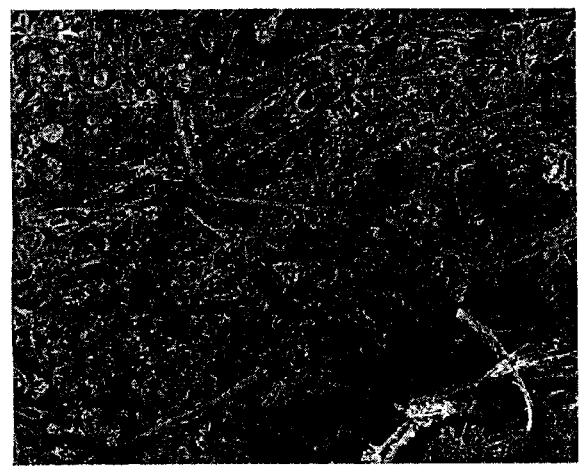
FIG. 20 is a SEM photograph illustrating a form of HepG2 cells cultured for 14 days on the culture carrier of Reference Example 3.
Figure 21:
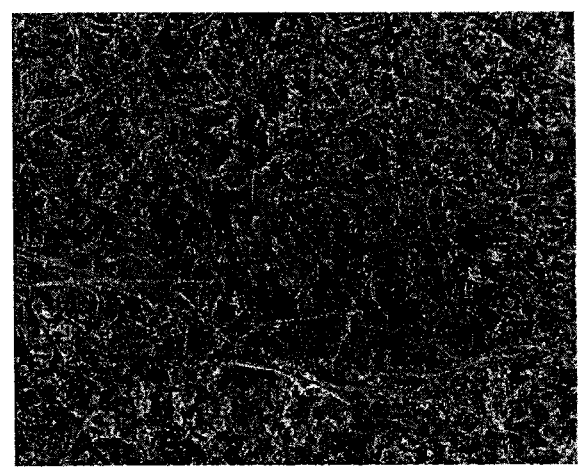
FIG. 21 is a SEM photograph illustrating a form of HepG2 cells cultured for 14 days on the culture carrier of Reference Example 4.

SEM photographs taken after the culture for 14 days are shown in FIG. 18 (Reference Example 1: unheated), FIG. 19 (Reference Example 2: heated at 100° C.), FIG. 20 (Reference Example 3: heated at 300° C.), and FIG. 21 (Reference Example 4: heated at 500° C.).

From the results illustrated in FIGS. 18 to 21, it was found that, when an amount of hydroxyl groups of the culture carrier is abundant and the hydrophilicity thereof is high, spheroid type of cells are easily cultured, and, when an amount of hydroxyl groups of the culture carrier is low and the hydrophobicity is high, sheet type of cells is easily cultured.

INDUSTRIAL APPLICABILITY

The inorganic fiber structure of the present invention can be applied to, for example, a heat insulating material, a filter material, an analysis tool, a culture carrier of such as cells, a catalyst carrier, antibacterial material and the like. The cell culture carrier can be applied to all fields that use the cell culture. Examples thereof include analysis tools, regenerative medicines, useful goods productions and the like, which use the cell culture.

Although the present invention has been described with reference to specific embodiments, various changes and modifications obvious to those skilled in the art are possible without departing from the scope of the appended claims.

The invention claimed is:

1. An inorganic fiber structure comprising electrospun inorganic fibers containing an inorganic compound and having an average fiber diameter of 3 µm or less,
    wherein the entirety of the structure, including its inside, is adhered with an inorganic adhesive consisting of the same inorganic component as that of the electrospun inorganic fibers, wherein the porosity of the inorganic fiber structure is 90% or more.

2. The inorganic fiber structure according to claim 1, wherein the structure has a tensile rupture strength of 0.2 MPa or more.

3. The inorganic fiber structure according to claim 1, wherein the amount of hydroxyl groups per unit weight of fiber is 50 µmol/g or more.

4. The inorganic fiber structure according to claim 1, further comprising an inorganic fiber aggregate produced by at least a step where inorganic fibers spun by an electrospinning method are irradiated with ions having a polarity opposite to that of the inorganic fibers to accumulate the inorganic fibers, and is adhered with an inorganic adhesive in an entirety including the inside thereof.

5. The inorganic fiber structure according to claim 1, wherein a film is not formed between the inorganic fibers.

6. The inorganic fiber structure according to claim 1, wherein a metal ion-containing compound is imparted to the inorganic fiber structure to give the structure functionality.

7. The inorganic fiber structure according to claim 1, which is used as a culture carrier.

8. A process for producing the inorganic fiber structure of claim 1, comprising:
    (i) spinning inorganic fibers by an electrospinning method from a spinning inorganic sol solution containing a compound mainly composed of an inorganic component;
    (ii) forming an inorganic fiber aggregate by irradiating the inorganic fibers with ions having a polarity opposite to that of the inorganic fibers to accumulate the inorganic fibers; and
    (iii) forming an inorganic fiber structure adhering to the inorganic fiber aggregate with an inorganic adhesive in an entirety including the inside thereof, where an adhering inorganic sol solution containing a compound mainly composed of an inorganic component is imparted to an entirety including the inside of the inorganic fiber aggregate, and an excess adhering inorganic sol solution is removed by gas-through.

9. The process for producing an inorganic fiber structure according to claim 8, wherein a heat treatment is conducted after the inorganic fiber aggregate is formed, in step (ii).

10. The process for producing an inorganic fiber structure according to claim 9, wherein a heat treatment temperature is 500° C. or less.

11. The process for producing an inorganic fiber structure according to claim 8, wherein after the excess adhering inorganic sol solution is removed by gas-through, a heat treatment is conducted, in (iii).

12. The process for producing an inorganic fiber structure according to claim 11, wherein a heat treatment temperature is 500° C. or less.

13. The process for producing an inorganic fiber structure according to claim 8, wherein the spinning inorganic sol solution and/or the adhering inorganic sol solution contains a metal ion-containing compound.

14. The process for producing an inorganic fiber structure according to claim 8, wherein after step (iii) is conducted, a solution containing a metal ion-containing compound is imparted to the inorganic fiber structure.

* * * * *